US012779174B2

(12) United States Patent
Roll et al.

(10) Patent No.: US 12,779,174 B2
(45) Date of Patent: Nov. 3, 2026

(54) MEDICAL DEVICES FOR INTERVENTIONAL MRI AND RELATED METHODS

(71) Applicant: Muffin Incorporated, West Lafayette, IN (US)

(72) Inventors: Jesse Roll, West Lafayette, IN (US); Andrew Robison, Otterbein, IN (US); Ram H. Paul, Jr., Bloomington, IN (US); Brent A. Mayle, Spencer, IN (US); Sean D. Chambers, Bloomington, IN (US); Neal E. Fearnot, West Lafayette, IN (US); Joshua Krieger, Topsfield, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 19/042,306

(22) Filed: Jan. 31, 2025

(65) Prior Publication Data

US 2025/0249212 A1 Aug. 7, 2025

Related U.S. Application Data

(60) Provisional application No. 63/550,545, filed on Feb. 6, 2024.

(51) Int. Cl.
*A61M 25/01* (2006.01)
*A61M 25/00* (2006.01)
(Continued)

(52) U.S. Cl.
CPC ...... *A61M 25/0127* (2013.01); *A61M 25/001* (2013.01); *A61M 25/0012* (2013.01);
(Continued)

(58) Field of Classification Search
CPC ............ A61M 25/0127; A61M 25/001; A61M 25/0012; A61M 25/0045; A61M 25/005;
(Continued)

(56) References Cited

U.S. PATENT DOCUMENTS

| | | | |
|---|---|---|---|
| 4,471,204 | A | 9/1984 | Takafuji |
| 4,781,186 | A | 11/1988 | Simpson |

(Continued)

FOREIGN PATENT DOCUMENTS

| | | |
|---|---|---|
| AT | 312640 | 12/2005 |
| AU | 2002334881 | 4/2003 |

(Continued)

OTHER PUBLICATIONS

International Application No. PCT/US2024/014660 International Search Report and Written Opinion, mailed Nov. 6, 2024.

(Continued)

*Primary Examiner* — Chao Sheng
(74) *Attorney, Agent, or Firm* — Woodard, Emhardt, Henry, Reeves & Wagner, LLP

(57) ABSTRACT

The disclosure relates to medical devices, methods of performing an interventional medical treatment under MRI, and methods of making a medical device. An example medical device includes an elongate member, a reinforcement member, and a marker. The elongate member has a proximal end, a distal end, and a circumferential wall having an outer surface and an inner surface that defines a lumen. The reinforcement member is disposed within the circumferential wall, extends along a length of the elongate member, is formed of a first material, and has a first susceptibility. The marker is attached to the elongate member, is formed of a second material, and has a second susceptibility that is different from the first susceptibility.

30 Claims, 12 Drawing Sheets

(51) Int. Cl.
*A61M 25/06* (2006.01)
*A61B 90/00* (2016.01)

(52) U.S. Cl.
CPC ...... *A61M 25/0045* (2013.01); *A61M 25/005* (2013.01); *A61M 25/0068* (2013.01); *A61M 25/0097* (2013.01); *A61M 25/0662* (2013.01); *A61B 2090/3954* (2016.02); *A61M 2025/006* (2013.01); *A61M 2025/0062* (2013.01); *A61M 2205/0216* (2013.01); *A61M 2205/0222* (2013.01); *A61M 2205/0233* (2013.01); *A61M 2205/0238* (2013.01); *A61M 2205/025* (2013.01); *A61M 2205/0266* (2013.01); *A61M 2207/00* (2013.01)

(58) Field of Classification Search
CPC .......... A61M 25/0068; A61M 25/0097; A61M 25/0662; A61M 2025/006; A61M 2025/0062; A61M 2025/0216; A61M 2025/0222; A61M 2025/0233; A61M 2025/0238; A61M 2025/025; A61M 2025/0266; A61M 2207/00; A61B 2090/3954
See application file for complete search history.

(56) References Cited

U.S. PATENT DOCUMENTS

| | | | |
|---|---|---|---|
| 4,862,891 | A | 9/1989 | Smith |
| 5,053,004 | A | 10/1991 | Markel |
| 5,169,396 | A | 12/1992 | Dowlatshahi |
| 5,228,441 | A | 7/1993 | Lundquist |
| 5,284,128 | A | 2/1994 | Hart |
| 5,291,890 | A | 3/1994 | Cline |
| 5,315,996 | A | 5/1994 | Lundquist |
| 5,322,064 | A | 6/1994 | Lundquist |
| 5,322,505 | A | 6/1994 | Krause |
| 5,329,923 | A | 7/1994 | Lundquist |
| 5,346,473 | A | 9/1994 | Bowman |
| 5,362,478 | A | 11/1994 | Desai |
| 5,380,304 | A | 1/1995 | Parker |
| 5,425,723 | A | 6/1995 | Wang |
| 5,454,787 | A | 10/1995 | Lundquist |
| 5,460,187 | A | 10/1995 | Daigle |
| 5,477,856 | A | 12/1995 | Lundquist |
| 5,507,766 | A | 4/1996 | Kugo |
| 5,573,520 | A | 11/1996 | Schwartz |
| 5,578,009 | A | 11/1996 | Kraus |
| 5,605,543 | A | 2/1997 | Swanson |
| 5,685,868 | A | 11/1997 | Lundquist |
| 5,690,120 | A | 11/1997 | Jacobsen |
| 5,728,079 | A | 3/1998 | Weber et al. |
| 5,730,732 | A | 3/1998 | Sardelis |
| 5,741,429 | A | 4/1998 | Donadio |
| 5,755,714 | A | 5/1998 | Murphy-Chutorian |
| 5,792,055 | A | 8/1998 | McKinnon |
| 5,813,996 | A | 9/1998 | St. Germain |
| 5,833,632 | A | 11/1998 | Jacobsen |
| 5,833,692 | A | 11/1998 | Cesarini |
| 5,853,375 | A | 12/1998 | Orr |
| 5,897,533 | A | 4/1999 | Glickman |
| 5,897,536 | A | 4/1999 | Nap |
| 5,908,410 | A | 6/1999 | Weber et al. |
| 5,910,807 | A | 6/1999 | Ueda |
| 5,916,162 | A | 6/1999 | Snelten |
| 5,922,003 | A | 7/1999 | Anctil |
| 5,951,494 | A | 9/1999 | Wang |
| 6,017,319 | A | 1/2000 | Jacobsen |
| 6,019,737 | A | 2/2000 | Murata |
| 6,059,769 | A | 5/2000 | Lunn |
| 6,091,385 | A | 7/2000 | Ellis |
| 6,102,890 | A | 8/2000 | Stivland |
| 6,146,373 | A | 11/2000 | Cragg |
| 6,228,073 | B1 | 5/2001 | Noone |
| 6,246,896 | B1 | 6/2001 | Dumoulin |
| 6,246,914 | B1 | 6/2001 | de la Rama et al. |
| 6,267,781 | B1 | 7/2001 | Tu |
| 6,273,404 | B1 | 8/2001 | Holman |
| 6,286,555 | B1 | 9/2001 | Pauker |
| 6,350,253 | B1 | 2/2002 | Deniega |
| 6,375,059 | B2 | 4/2002 | Ohnishi |
| 6,394,976 | B1 | 5/2002 | Winston |
| 6,428,489 | B1 | 8/2002 | Jacobsen |
| 6,451,026 | B1 | 9/2002 | Biagtan |
| 6,458,088 | B1 | 10/2002 | Hurtak |
| 6,464,645 | B1 | 10/2002 | Park |
| 6,574,497 | B1 | 6/2003 | Pacetti |
| 6,611,720 | B2 | 8/2003 | Hata |
| 6,612,998 | B2 | 9/2003 | Gosiengfiao |
| 6,613,002 | B1 | 9/2003 | Clark et al. |
| 6,623,491 | B2 | 9/2003 | Thompson |
| 6,626,849 | B2 | 9/2003 | Huitema |
| 6,652,508 | B2 | 11/2003 | Griffin |
| 6,675,033 | B1 | 1/2004 | Lardo |
| 6,687,533 | B1 | 2/2004 | Hirano |
| 6,695,781 | B2 | 2/2004 | Rabiner |
| 6,714,809 | B2 | 3/2004 | Lee |
| 6,749,560 | B1 | 6/2004 | Konstorum |
| 6,772,000 | B2 | 8/2004 | Talpade |
| 6,799,067 | B2 | 9/2004 | Pacetti |
| 6,845,259 | B2 | 1/2005 | Pacetti |
| 6,860,898 | B2 | 3/2005 | Stack |
| 6,911,016 | B2 | 6/2005 | Balzum |
| 6,918,882 | B2 | 7/2005 | Skujins |
| 6,975,896 | B2 | 12/2005 | Ehnholm |
| 7,001,369 | B2 | 2/2006 | Griffin |
| 7,074,197 | B2 | 7/2006 | Reynolds |
| 7,160,296 | B2 | 1/2007 | Pearson |
| 7,169,118 | B2 | 1/2007 | Reynolds |
| 7,182,735 | B2 | 2/2007 | Shireman |
| 7,278,973 | B2 | 10/2007 | Iwami |
| 7,347,829 | B2 | 3/2008 | Mark |
| 7,507,211 | B2 | 3/2009 | Pacetti |
| 7,540,845 | B2 | 6/2009 | Parins |
| 7,553,287 | B2 | 6/2009 | Reynolds |
| 7,596,402 | B2 | 9/2009 | Duerk |
| 7,618,379 | B2 | 11/2009 | Reynolds |
| 7,641,621 | B2 | 1/2010 | Crank |
| 7,651,578 | B2 | 1/2010 | Sharrow |
| 7,708,751 | B2 | 5/2010 | Hughes |
| 7,747,314 | B2 | 6/2010 | Parins |
| 7,749,264 | B2 | 7/2010 | Gregorich |
| 7,758,520 | B2 | 7/2010 | Griffin |
| 7,761,138 | B2 | 7/2010 | Wang |
| 7,778,682 | B2 | 8/2010 | Kumar |
| 7,785,273 | B2 | 8/2010 | Eskuri |
| 7,789,906 | B2 | 9/2010 | Blank |
| 7,792,568 | B2 | 9/2010 | Zhong |
| 7,833,175 | B2 | 11/2010 | Parins |
| 7,841,994 | B2 | 11/2010 | Skujins |
| 7,848,788 | B2 | 12/2010 | Tulley |
| 7,875,025 | B2 | 1/2011 | Cockburn |
| 7,914,467 | B2 | 3/2011 | Layman |
| 7,918,819 | B2 | 4/2011 | Karmarkar |
| 7,943,161 | B2 | 5/2011 | Carlgren |
| 7,989,042 | B2 | 8/2011 | Obara |
| 7,993,286 | B2 | 8/2011 | Reynolds |
| 8,002,715 | B2 | 8/2011 | Shireman |
| 8,007,434 | B2 | 8/2011 | Olson |
| 8,021,311 | B2 | 9/2011 | Munoz |
| 8,048,004 | B2 | 11/2011 | Davis |
| 8,048,030 | B2 | 11/2011 | McGuckin, Jr. |
| 8,049,137 | B2 | 11/2011 | Holman |
| 8,067,073 | B2 | 11/2011 | Zhong |
| 8,070,693 | B2 | 12/2011 | Ayala |
| 8,082,021 | B2 | 12/2011 | Hyde |
| 8,092,444 | B2 | 1/2012 | Lentz |
| 8,105,246 | B2 | 1/2012 | Voeller |
| 8,137,292 | B2 | 3/2012 | Skujins |
| 8,137,293 | B2 | 3/2012 | Zhou |
| 8,142,431 | B2 | 3/2012 | Ducharme |
| 8,163,326 | B2 | 4/2012 | Zhong |
| 8,167,815 | B2 | 5/2012 | Parihar |

(56) References Cited

U.S. PATENT DOCUMENTS 8,167,821 B2 5/2012 Sharrow
8,182,444 B2 5/2012 Uber, III
8,182,465 B2 5/2012 Griffin
8,211,116 B2 7/2012 Oostman, Jr.
8,211,143 B2 7/2012 Stefanchik
8,214,015 B2 7/2012 Macaulay
8,257,279 B2 9/2012 Davis
8,257,358 B2 9/2012 Haddock
8,262,563 B2 9/2012 Bakos
8,292,827 B2 10/2012 Musbach
8,292,828 B2 10/2012 Uihlein
8,337,492 B2 12/2012 Kunis
8,376,961 B2 2/2013 Layman
8,396,532 B2 3/2013 Jenkins
8,409,114 B2 4/2013 Parins
8,414,506 B2 4/2013 Reynolds
8,419,658 B2 4/2013 Eskuri
8,478,381 B2 7/2013 Kocaturk
8,485,992 B2 7/2013 Griffin
8,521,257 B2 8/2013 Whitcomb
8,523,786 B2 9/2013 Von Weymarn-Scharli
8,526,691 B2 9/2013 Strehl
8,529,872 B2 9/2013 Frank
8,535,243 B2 9/2013 Shireman
8,535,310 B2 9/2013 Hardin
8,540,648 B2 9/2013 Uihlein
8,551,020 B2 10/2013 Chen
8,551,021 B2 10/2013 Voeller
8,556,914 B2 10/2013 Vrba
8,620,406 B2 12/2013 Smith
8,636,716 B2 1/2014 Griffin
8,684,953 B2 4/2014 Cabiri
8,728,010 B2 5/2014 Hirshman
8,728,116 B1 5/2014 Janardhan
8,740,957 B2 6/2014 Masotti
8,795,202 B2 8/2014 Northrop
8,795,254 B2 8/2014 Layman
8,846,006 B2 9/2014 Frank
8,880,149 B2 11/2014 Barbot
8,932,270 B2 1/2015 O'Day
9,038,639 B2 5/2015 Pfeffer et al.
9,072,874 B2 7/2015 Northrop
9,138,561 B2 9/2015 Stenzel
9,192,743 B2 11/2015 Stenzel
9,227,037 B2 1/2016 Northrop
9,326,757 B2 5/2016 Ravikumar
9,346,093 B2 5/2016 Cacace
9,375,195 B2 6/2016 Kamen
9,383,421 B2 7/2016 Vij
9,656,004 B2 5/2017 Duering
9,669,240 B2 6/2017 Kohler
9,687,681 B2 6/2017 Kohler
9,775,523 B2 10/2017 Gregorich
9,861,450 B2 1/2018 Bolan
10,010,723 B2 7/2018 Koehler
10,028,666 B2 7/2018 Gregorich
10,035,002 B2 7/2018 Weiss
10,065,023 B2 9/2018 Sela
10,172,537 B2 1/2019 Pfeffer
10,201,333 B2 2/2019 Nock
10,555,753 B2 2/2020 Moberg
10,555,756 B2 2/2020 Krieger
10,695,540 B2 6/2020 Kocaturk
10,814,044 B2 10/2020 Duering
10,835,710 B2 11/2020 Lederman
10,953,195 B2 3/2021 Jalgaonkar et al.
10,976,388 B2 4/2021 Yang
11,034,580 B2 6/2021 Ostrovska
11,052,242 B1 7/2021 Gore
11,062,473 B2 7/2021 Fine
11,071,869 B2 7/2021 Leigh
11,090,033 B2 8/2021 Rebellino
11,090,130 B2 8/2021 Nemanic
11,097,017 B2 8/2021 Preihs
11,105,873 B2 8/2021 Poole
11,116,405 B2 9/2021 Partanen
11,142,826 B2 10/2021 Han
11,202,888 B2 12/2021 Paul, Jr.
11,219,761 B2 1/2022 Verzal
11,226,383 B2 1/2022 Sengupta
11,234,654 B2 2/2022 Han
11,241,296 B2 2/2022 Bolan
11,260,222 B2 3/2022 Olsen
11,266,326 B2 3/2022 Dyer
11,298,567 B2 4/2022 Vahala
11,304,683 B2 4/2022 Mitra
11,318,280 B2 5/2022 Weiss
11,737,851 B2 8/2023 Paul
2002/0055449 A1 5/2002 Porta
2002/0058868 A1 5/2002 Hoshino
2002/0107446 A1 8/2002 Rabiner
2002/0151787 A1 10/2002 Bjornerud
2003/0055332 A1 3/2003 Daum
2003/0055449 A1 3/2003 Lee
2003/0060731 A1 3/2003 Fleischhacker
2003/0060842 A1 3/2003 Chin
2003/0069520 A1 4/2003 Skujins
2003/0069521 A1 4/2003 Reynolds
2003/0100828 A1 5/2003 Engelhard
2003/0100829 A1 5/2003 Zhong et al.
2003/0120148 A1 6/2003 Pacetti
2003/0135114 A1 7/2003 Pacetti
2003/0167052 A1 9/2003 Lee
2003/0187461 A1 10/2003 Chin
2003/0208142 A1 11/2003 Boudewijn
2004/0082946 A1 4/2004 Malis
2004/0082948 A1 4/2004 Stewart
2004/0097880 A1 5/2004 Schur
2004/0143180 A1 7/2004 Zhong
2004/0167428 A1 8/2004 Quick et al.
2004/0167437 A1 8/2004 Sharrow
2004/0167438 A1 8/2004 Sharrow
2004/0167439 A1 8/2004 Sharrow
2004/0167442 A1 8/2004 Shireman et al.
2004/0186377 A1 9/2004 Zhong et al.
2004/0193140 A1 9/2004 Griffin
2004/0199240 A1 10/2004 Dorn
2004/0200881 A1 10/2004 Gandy
2004/0254445 A1 12/2004 Bittner
2004/0254450 A1 12/2004 Griffin
2005/0021002 A1 1/2005 Deckman
2005/0054952 A1 3/2005 Eskuri
2005/0065437 A1 3/2005 Weber
2005/0070793 A1 3/2005 Pacetti
2005/0096665 A1 5/2005 Reynolds
2005/0119615 A1 6/2005 Noriega
2005/0125053 A1 6/2005 Yachia
2005/0143650 A1 6/2005 Winkel
2005/0148865 A1 7/2005 Weber
2005/0149009 A1 7/2005 Wakikaido
2005/0165301 A1 7/2005 Smith
2005/0215874 A1 9/2005 Wang
2005/0240165 A1 10/2005 Miki
2005/0277829 A1 12/2005 Tsonton
2005/0283215 A1 12/2005 Desinger et al.
2006/0004346 A1 1/2006 Begg
2006/0073101 A1 4/2006 Oldfield
2006/0100687 A1 5/2006 Fahey
2006/0122537 A1 6/2006 Reynolds
2006/0200048 A1 9/2006 Furst
2006/0253178 A1 11/2006 Masotti
2007/0016131 A1 1/2007 Munger
2007/0026555 A1 2/2007 Lee
2007/0043333 A1 2/2007 Kampa et al.
2007/0060878 A1 3/2007 Bonnette
2007/0083132 A1 4/2007 Sharrow
2007/0112331 A1 5/2007 Weber
2007/0135734 A1 6/2007 Reynolds
2007/0149037 A1 6/2007 Souba
2007/0162108 A1 7/2007 Carlson
2007/0208405 A1 9/2007 Goodin
2007/0244414 A1 10/2007 Reynolds
2007/0265551 A1 11/2007 Pfister
2007/0280850 A1 12/2007 Carlson

(56) References Cited

U.S. PATENT DOCUMENTS

2008/0004689 A1 1/2008 Jahnke
2008/0021313 A1 1/2008 Eidenschink
2008/0021347 A1 1/2008 Jacobsen
2008/0021400 A1 1/2008 Jacobsen
2008/0021401 A1 1/2008 Jacobsen
2008/0021402 A1 1/2008 Jacobsen
2008/0021403 A1 1/2008 Jacobsen
2008/0021405 A1 1/2008 Jacobsen
2008/0021406 A1 1/2008 Jacobsen
2008/0021407 A1 1/2008 Jacobsen
2008/0021408 A1 1/2008 Jacobsen
2008/0045908 A1 2/2008 Gould
2008/0077085 A1 3/2008 Eidenschink
2008/0086047 A1 4/2008 McDaniel
2008/0097294 A1 4/2008 Prather
2008/0097395 A1 4/2008 Adams
2008/0097398 A1 4/2008 Mitelberg
2008/0097404 A1 4/2008 Yribarren
2008/0125674 A1 5/2008 Bilecen
2008/0125766 A1 5/2008 Lubock
2008/0139925 A1 6/2008 Lubock
2008/0147001 A1 6/2008 Al-Marashi
2008/0194994 A1 8/2008 Bown
2008/0195194 A1 8/2008 Pacetti
2008/0262474 A1 10/2008 Northrop
2008/0269641 A1 10/2008 O'Shaughnessy et al.
2008/0272774 A1 11/2008 Bieri
2008/0294231 A1 11/2008 Aguilar
2008/0312597 A1 12/2008 Uihlein
2009/0036832 A1 2/2009 Skujins
2009/0043228 A1 2/2009 Northrop
2009/0043283 A1 2/2009 Turnlund
2009/0043372 A1 2/2009 Northrop
2009/0117711 A1 5/2009 Harle
2009/0118675 A1 5/2009 Czyscon
2009/0118704 A1 5/2009 Sharrow
2009/0177040 A1 7/2009 Lyons
2009/0177119 A1 7/2009 Heidner
2009/0192584 A1 7/2009 Gerdts
2009/0227901 A1 9/2009 Hofmann
2009/0264731 A1 10/2009 Sugiura
2009/0292225 A1 11/2009 Chen
2010/0004562 A1 1/2010 Jalisi
2010/0030072 A1 2/2010 Casanova
2010/0036364 A1 2/2010 Wuebbeling
2010/0063383 A1 3/2010 Anderson et al.
2010/0063479 A1 3/2010 Merdan
2010/0069882 A1 3/2010 Jennings
2010/0087849 A1 4/2010 Griffin
2010/0145308 A1 6/2010 Layman
2010/0152612 A1 6/2010 Headley, Jr.
2010/0185080 A1 7/2010 Myhr
2010/0201361 A1 8/2010 Edelman
2010/0207291 A1 8/2010 Eidenschink
2010/0254897 A1 10/2010 Frank
2010/0268325 A1 10/2010 Gregorich
2011/0022069 A1 1/2011 Mitusina
2011/0098554 A1 4/2011 Mardor
2011/0160834 A1 6/2011 Aggerholm
2011/0166439 A1 7/2011 Pfeffer
2011/0251519 A1 10/2011 Romoscanu
2011/0270169 A1 11/2011 Gardeski
2011/0276034 A1 11/2011 Tomarelli
2012/0035434 A1 2/2012 Ferren
2012/0053419 A1 3/2012 Bloom
2012/0053572 A1 3/2012 Rusu
2012/0078087 A1 3/2012 Curry
2012/0083877 A1 4/2012 Nguyen et al.
2012/0108881 A1 5/2012 Chi Sing et al.
2012/0157935 A1 6/2012 Wueebbeling
2012/0172841 A1 7/2012 Kubo et al.
2012/0232658 A1 9/2012 Morgenstern et al.
2012/0265229 A1 10/2012 Rottenberg
2012/0289776 A1 11/2012 Keast
2013/0030362 A1 1/2013 Wright
2013/0046285 A1 2/2013 Griffin
2013/0072904 A1 3/2013 Musbach
2013/0085444 A1 4/2013 Heinrich
2013/0123692 A1 5/2013 Zhang
2013/0123768 A1 5/2013 Harlan
2013/0131496 A1 5/2013 Jenkins et al.
2013/0158478 A1 6/2013 Kaufmann
2013/0165942 A1 6/2013 Tan-Malecki
2013/0231586 A1 9/2013 Tsonton
2013/0274591 A1 10/2013 Sonmez
2013/0274618 A1 10/2013 Hou et al.
2013/0274711 A1 10/2013 O'Day
2013/0296718 A1 11/2013 Ranganathan
2013/0296903 A1 11/2013 Nita
2013/0304035 A1 11/2013 Cabiri
2013/0324837 A1 12/2013 Meyer
2014/0005558 A1 1/2014 Gregorich
2014/0005647 A1 1/2014 Shuffler
2014/0031843 A1 1/2014 Rottenberg
2014/0053940 A1 2/2014 Konstorum
2014/0058275 A1 2/2014 Gregorich
2014/0081134 A1 3/2014 Fortson
2014/0081244 A1 3/2014 Voeller
2014/0121590 A1 5/2014 Degen
2014/0121642 A1 5/2014 Jordan
2014/0180302 A1 6/2014 Vetter et al.
2014/0243615 A1 8/2014 Schaeffer
2014/0243742 A1 8/2014 Pacheco
2014/0350414 A1 11/2014 McGowan
2014/0378946 A1 12/2014 Simpson
2015/0011834 A1 1/2015 Ayala
2015/0051583 A1 2/2015 Horvath
2015/0051696 A1 2/2015 Hou
2015/0073391 A1 3/2015 Hutchins
2015/0083284 A1 3/2015 Rawson
2015/0105796 A1 4/2015 Grace
2015/0148706 A1 5/2015 Abner
2015/0151081 A1 6/2015 Keith
2015/0182671 A1 7/2015 During
2015/0190614 A1 7/2015 Uihlein
2015/0209551 A1 7/2015 Burdette
2015/0265167 A1 9/2015 McGowan
2015/0335391 A1 11/2015 Linderman
2015/0338477 A1 11/2015 Schmidt
2015/0342580 A1 12/2015 Clancy
2015/0351644 A1 12/2015 Lee
2015/0374929 A1 12/2015 Hyde
2016/0008584 A1 1/2016 Root
2016/0033059 A1 2/2016 Fonte
2016/0045190 A1 2/2016 Elfman
2016/0051384 A1 2/2016 Patel
2016/0051798 A1 2/2016 Weber
2016/0082228 A1 3/2016 Sela
2016/0089515 A1 3/2016 Hansen
2016/0158509 A1 6/2016 Wedan
2016/0317212 A1 11/2016 Ge et al.
2017/0055908 A1 3/2017 Radman
2017/0106171 A1* 4/2017 Flores .................. A61M 25/09
2017/0143317 A1 5/2017 Hoffman
2017/0165456 A1 6/2017 Tutungi
2017/0202480 A1 7/2017 Kim et al.
2017/0232158 A1 8/2017 During
2017/0239450 A1 8/2017 Kocaturk
2017/0291013 A1 10/2017 Pereira
2017/0347913 A1 12/2017 Isaacson et al.
2017/0348509 A1 12/2017 Burkholz
2018/0078742 A1 3/2018 Butler
2018/0078743 A1 3/2018 Kubo et al.
2018/0085027 A1 3/2018 Kimmel
2018/0085184 A1 3/2018 Bolan
2018/0140801 A1 5/2018 Voss
2018/0161121 A1 6/2018 Butler
2018/0185618 A1 7/2018 Sweeney
2018/0193606 A1 7/2018 Patel
2018/0193608 A1 7/2018 Bodewadt
2018/0243530 A1 8/2018 Lederman
2018/0289388 A1 10/2018 Lenker
2018/0303603 A1 10/2018 Melsheimer
2019/0046684 A1 2/2019 Roth

(56) References Cited

U.S. PATENT DOCUMENTS

| | | | | |
|---|---|---|---|---|
| 2019/0083071 | A1 | 3/2019 | Rebellino | |
| 2019/0167952 | A1 | 6/2019 | Paul, Jr. | |
| 2019/0192124 | A1 | 6/2019 | Park | |
| 2019/0223975 | A1 | 7/2019 | Agostinelli et al. | |
| 2019/0351182 | A1 | 11/2019 | Chou et al. | |
| 2019/0366036 | A1* | 12/2019 | Jalgaonkar .......... | A61M 25/008 |
| 2019/0374279 | A1 | 12/2019 | Weitzner | |
| 2020/0000545 | A1 | 1/2020 | Paul | |
| 2020/0008678 | A1 | 1/2020 | Barbagli et al. | |
| 2020/0069927 | A1 | 3/2020 | Malek | |
| 2020/0121415 | A1 | 4/2020 | Mayes et al. | |
| 2021/0077077 | A1 | 3/2021 | Mitra et al. | |
| 2021/0106791 | A1 | 4/2021 | Uihlein | |
| 2021/0177510 | A1 | 6/2021 | Papioannou | |
| 2021/0178121 | A1 | 6/2021 | Burdette | |
| 2021/0187253 | A1 | 6/2021 | Borm | |
| 2021/0208225 | A1 | 7/2021 | Gilbo | |
| 2021/0220624 | A1 | 7/2021 | Blacker | |
| 2021/0228841 | A1 | 7/2021 | Falb | |
| 2021/0236017 | A1 | 8/2021 | Pfeffer | |
| 2021/0247472 | A1 | 8/2021 | Kocaturk et al. | |
| 2021/0251696 | A1 | 8/2021 | Krueckers | |
| 2021/0255261 | A1 | 8/2021 | Piferi | |
| 2021/0267696 | A1 | 9/2021 | Degertekin et al. | |
| 2021/0275155 | A1 | 9/2021 | Hautvast et al. | |
| 2021/0282866 | A1 | 9/2021 | Vij | |
| 2021/0295985 | A1 | 9/2021 | Prokle | |
| 2022/0015636 | A1 | 1/2022 | Mak et al. | |
| 2022/0050154 | A1 | 2/2022 | Schneider | |
| 2022/0088353 | A1 | 3/2022 | Paul, Jr. | |
| 2022/0096116 | A1 | 3/2022 | McFarland et al. | |
| 2022/0101576 | A1 | 3/2022 | Kaushik | |
| 2022/0104913 | A1 | 4/2022 | Blair | |
| 2022/0218881 | A1 | 7/2022 | Cook et al. | |
| 2023/0248241 | A1* | 8/2023 | Anttila ............... | A61B 10/0233<br>600/411 |

FOREIGN PATENT DOCUMENTS

| | | | |
|---|---|---|---|
| AU | 2002358281 | | 7/2003 |
| CA | 2094250 | | 6/1992 |
| CA | 2462335 | | 4/2003 |
| CN | 2930741 | | 8/2007 |
| CN | 106943218 | | 7/2017 |
| CN | 112426611 | | 3/2021 |
| DE | 19843427 | | 3/2000 |
| DE | 20019484 | | 5/2001 |
| DE | 10029738 | | 1/2002 |
| DE | 20017836 | | 2/2002 |
| DE | 10243261 | | 3/2004 |
| DE | 60208057 | | 6/2006 |
| DE | 102005022688 | | 11/2006 |
| DE | 102005030472 | A1 | 1/2007 |
| DE | 202010004107 | | 6/2010 |
| DE | 202010016473 | | 2/2012 |
| DE | 102011101680 | | 9/2012 |
| DE | 102011081445 | | 2/2013 |
| EP | 0315290 | | 5/1989 |
| EP | 0561903 | | 9/1993 |
| EP | 0628288 | | 12/1994 |
| EP | 0561903 | B1 | 7/1995 |
| EP | 0744186 | | 11/1996 |
| EP | 0775500 | | 5/1997 |
| EP | 0937481 | | 8/1999 |
| EP | 0628288 | B1 | 4/2000 |
| EP | 1011491 | | 6/2000 |
| EP | 1116476 | | 7/2001 |
| EP | 1116476 | A2 | 7/2001 |
| EP | 4008388 | A1 | 6/2002 |
| EP | 1242138 | | 9/2002 |
| EP | 1432467 | | 6/2004 |
| EP | 1551490 | | 7/2005 |
| EP | 1596894 | | 11/2005 |
| EP | 1656963 | A1 | 5/2006 |
| EP | 1819374 | | 8/2007 |
| EP | 2228094 | A1 | 9/2010 |
| EP | 2364746 | | 9/2011 |
| EP | 2508213 | A1 | 10/2012 |
| EP | 2675353 | | 12/2013 |
| EP | 2762189 | A1 | 8/2014 |
| EP | 3093037 | | 11/2016 |
| EP | 2508213 | B1 | 3/2018 |
| EP | 3288629 | | 3/2018 |
| EP | 3349650 | | 7/2018 |
| EP | 3586763 | A2 | 1/2020 |
| EP | 3610913 | A1 | 2/2020 |
| EP | 3586763 | A3 | 3/2020 |
| JP | 6032553 | | 7/1985 |
| JP | H10248853 | | 9/1998 |
| JP | H10290839 | | 11/1998 |
| JP | H10314137 | | 12/1998 |
| JP | H11285533 | | 10/1999 |
| JP | 2005528126 | | 9/2005 |
| JP | 2005334645 | | 12/2005 |
| JP | 2006501974 | | 1/2006 |
| JP | 2006520645 | | 9/2006 |
| JP | 3962724 | | 8/2007 |
| JP | 2008515563 | | 5/2008 |
| JP | 2008272464 | | 11/2008 |
| JP | 2009512475 | | 3/2009 |
| JP | 2009183765 | | 8/2009 |
| JP | 2010517722 | | 5/2010 |
| JP | 4494782 | | 6/2010 |
| JP | 2020022737 | | 2/2020 |
| NL | 1006612 | | 1/1999 |
| WO | WO 9011313 | | 10/1990 |
| WO | WO 9842268 | | 10/1998 |
| WO | WO 9855016 | | 12/1998 |
| WO | WO 0007652 | | 2/2000 |
| WO | WO 2000064003 | | 10/2000 |
| WO | WO 01045786 | | 6/2001 |
| WO | WO 0195794 | | 12/2001 |
| WO | WO 2002055146 | | 7/2002 |
| WO | WO 03003982 | | 1/2003 |
| WO | WO 03030982 | | 4/2003 |
| WO | WO 03057302 | | 7/2003 |
| WO | WO 2003057302 | | 7/2003 |
| WO | WO 03092791 | | 11/2003 |
| WO | WO 2004075941 | | 9/2004 |
| WO | WO 2005112778 | | 12/2005 |
| WO | WO 2006036786 | | 4/2006 |
| WO | WO2006063106 | A1 | 6/2006 |
| WO | WO 2006116538 | | 11/2006 |
| WO | WO 2006119645 | | 11/2006 |
| WO | WO 2007045913 | | 4/2007 |
| WO | WO 2010103762 | A1 | 9/2010 |
| WO | WO 2011008538 | | 1/2011 |
| WO | WO 2012032881 | | 3/2012 |
| WO | WO 2012112829 | | 8/2012 |
| WO | WO 2016064753 | | 4/2016 |
| WO | WO 2016175882 | | 11/2016 |
| WO | WO 2016176393 | | 11/2016 |
| WO | WO 2017048759 | | 3/2017 |
| WO | WO 2018182701 | A1 | 10/2018 |
| WO | WO 2021081079 | | 4/2021 |
| WO | WO 2023150775 | A1 | 8/2023 |

OTHER PUBLICATIONS

Basar et al., "Segmented nitinol guidewires with stiffness-match connectors for cardiovascular magnetic resonance catheterization: preserved mechanical performance and freedom from heating", J. Cardiovascular Magnetic Resonance (2015), pp. 1-9.

Basar et al., "Susceptibility artifacts from metallic markers and cardiac catheterization devices on a high-performance 0.55 T MRI system", Magnetic Resonance Imaging, (2021), vol. 77, pp. 14-20.

Campbell-Washburn et al., "Opportunities in interventional and diagnostic imaging by using high-performance low-field-strength MRI", Radiology, (2019), vol. 293, No. 2, pp. 384-393.

Carpenter Corp. "Magnetic Properties of Stainless Steels," pp. 1-9. Retrieved from Internet May 3, 2018.

(56) References Cited

OTHER PUBLICATIONS

Cross et al., "Nitinol Characterization Study," Issued by Originator as Report No. GER-14188, (1969), NASA CR-1433, pp. 1-60.
Dempsey et al., "Investigation of the factors responsible for burns during MRI", Journal of Magnetic Resonance imaging: An Official Journal of the International Society for Magnetic Resonance in Medicine, (2001), vol. 13, No. 4, pp. 627-631.
Etezadi-Amoli et al., "Controlling radiofrequency-induced currents in guidewires using parallel transmit", Magnetic resonance in medicine, (2015), vol. 74, No. 6, pp. 1790-1802.
European Communication Examination Report, Application No. 17178169.3, dated Aug. 7, 2019.
European Communication pursuant to Article 94(3) EPC, Application No. 18829568.7, dated Jan. 30, 2024.
European Communication pursuant to Article 94(3) EPC, Application No. 18829568.7, dated Mar. 24, 2022.
European Communication pursuant to Article 94(3) EPC, Application No. 19183472.0, dated Nov. 11, 2021.
European Communication pursuant to Article 94(3), Application No. 23718542.6, dated Dec. 9, 2025.
European Communication pursuant to Article 96(2) EPC, Application No. 01942159.3, dated Jun. 14, 2006.
European Communication pursuant to Rule 161(1) and 162 EPC, Application No. 23713226.1, dated Sep. 17, 2024.
European extended Search Report, Application No. 17178169.3, dated Nov. 13, 2017.
European extended Search Report, Application No. 19183472.0, dated Feb. 13, 2020.
European extended Search report, Application No. 22150984.7, dated Dec. 5, 2022.
European Partial Search Report, Application No. 19183472.0, mailed Nov. 6, 2019.
European Partial Search Report, Application No. 22150984.7, dated Aug. 26, 2022.
European Patent Office Communication pursuant to Article 94(3), Application No. 23 718 542.6, dated May 16, 2025.
European Patent Office. "Supplementary European Serach Report" Application No. 01942159.3, completed Feb. 2, 2006.
European Supplementary Search Report, Application No. 01942159.3, completed Feb. 10, 2006.
Fichtinger et al., "Transrectal Prostate Biopsy Inside Closed MRI Scanner with Remote Actuation, under Real-Time Image Guidance", MICCAI, (2002), 5th International Conference, Tokyo, Japan, pp. 91-98.
Google Patents Translation of Chinese Application No. CN106943218A, retained from the Internet, May 23, 2024.
HiWire, Nitinal Core Wire Guide: Data Sheet, "Gain ureteral access with control.", Cook (2013).
Internation Search Report and Written Opinion, Application No. PCT/US2023/062094, dated May 9, 2023.
Japanese 1st Office Action, Application No. 2019-121677, dated Apr. 18, 2023.
Japanese Notification of Reason for Rejection, Application No. 2023-139741, mailed Jan. 8, 2025.
Japanese Notification of Refusal, Application No. 2022002110, dated Oct. 8, 2025.
Japanese Office Action, Application No. 2023139741, dated May 7, 2024.
Koniings et al., "Heating around intravascular guidewires by resonating RF waves", Journal of Magnetic Resonance Imaging, (2000), vol. 12, pp. 79-85.
Nano4Imaging, Your Health—Our Vision, MR wire guidewire: Technical Specification, retrieved from Internet on Sep. 6, 2023, URL: https://www.nano4imaging.com/#EmeryGlide.
Nour et al., "Magnetic Resonance Image-Guided Focal Prostate Ablation", Seminars in Interventional Radiology, (2016), vol. 33, No. 3, pp. 206-216.
PCT International Search Report and Written Opinion, Application No. PCT/US2016/029661, dated Jul. 27, 2016.
PCT International Search Report and Written Opinion, Application No. PCT/US2016/029670, dated Jul. 15, 2016.
PCT International Search Report and Written Opinion, Application No. PCT/US2018/063562, mailed Sep. 26, 2019.
PCT International Search Report and Written Opinion, Application No. PCT/US2023/030307, dated Dec. 18, 2023.
PCT International Search Report and Written Opinion, Application No. PCT/US2023/062094, dated Nov. 10, 2023.
PCT International Search Report and Written Opinion, Application No. PCT/US2023/062097, dated Jul. 13, 2023.
PCT International Search Report and Written Opinion, Application No. PCT/US2023/062104, dated Jul. 14, 2023.
PCT International Search Report and Written Opinion, Application No. PCT/US2024/014660, dated Nov. 6, 2024.
Tong et al., "Practical aspects of MR imaging in the presence of conductive guide wires", Physics in Medicine & Biology, (2009), vol. 55, No. 1, Abstract Only.
U.S. Office Action (Ex Parte Quayle) U.S. Appl. No. 16/454,905, dated Mar. 2, 2023.
U.S. Office Action (Final Rejection) U.S. Appl. No. 17/573,073, dated Jul. 22, 2024.
U.S. Office Action (Final Rejection) for U.S. Appl. No. 18/106,601, dated Jun. 2, 2025.
U.S. Office Action (Final Rejection) for U.S. Appl. No. 18/238,747, dated Dec. 16, 2025.
U.S. Office Action (Final Rejection) for U.S. Appl. No. 18/836,215, mailed Jan. 2, 2026.
U.S. Office Action (Final), U.S. Appl. No. 17/573,104, dated May 30, 2024.
U.S. Office Action (Final), U.S. Appl. No. 17/573,189, dated Dec. 19, 2024.
U.S. Office Action (Non-Final OA) U.S. Appl. No. 18/836,215, dated Jul. 24, 2025.
U.S. Office Action (Non-Final Rejection) U.S. Appl. No. 18/238,747, dated Jul. 1, 2025.
U.S. Office Action (Non-Final Rejection) for U.S. Appl. No. 17/573,073, mailed Dec. 3, 2025.
U.S. Office Action (Non-Final Rejection) for U.S. Appl. No. 17/573,087, dated Apr. 22, 2025.
U.S. Office Action (Non-Final Rejection) for U.S. Appl. No. 17/573,189, dated May 14, 2025.
U.S. Office Action (Non-Final Rejection) for U.S. Appl. No. 18/106,601, dated Jan. 9, 2026.
U.S. Office Action (Non-Final Rejection) for U.S. Appl. No. 18/234,440, dated Aug. 27, 2025.
U.S. Office Action (Non-Final Rejection) for U.S. Appl. No. 18/923,852, mailed Nov. 3, 2025.
U.S. Office Action (Non-Final Rejection) for U.S. Appl. No. 19/027,914, dated Dec. 18, 2025.
U.S. Office Action (Non-Final Rejection), U.S. Appl. No. 17/573,073, dated Dec. 17, 2024.
U.S. Office Action (Non-Final Rejection), U.S. Appl. No. 17/573,073, dated Jan. 31, 2024.
U.S. Office Action (Non-Final Rejection), U.S. Appl. No. 18/106,601, dated Nov. 18, 2024.
U.S. Office Action (Non-Final) U.S. Appl. No. 18/238,747, dated Mar. 14, 2025.
U.S. Office Action (Non-Final), U.S. Appl. No. 16/207,391, dated Feb. 19, 2021.
U.S. Office Action (Non-Final), U.S. Appl. No. 16/454,905, dated Oct. 13, 2022.
U.S. Office Action (Non-Final), U.S. Appl. No. 17/539,683, dated Dec. 8, 2022.
U.S. Office Action (Non-Final), U.S. Appl. No. 17/573,104, dated Dec. 22, 2023.
U.S. Office Action (Non-Final), U.S. Appl. No. 17/573,189, dated Jun. 24, 2024.
U.S. Office Action (Non-Final), U.S. Appl. No. 18/233,519, dated Mar. 5, 2024.
U.S. Office Action (Notice of Allowance and Fees Due (PTOL-85) for U.S. Appl. No. 17/573,073, dated Jun. 10, 2025.
U.S. Office Action (Notice of Allowance), U.S. Appl. No. 17/539,683, dated Mar. 31, 2023.

(56) References Cited

OTHER PUBLICATIONS

U.S. Office Action (Response Non-Final Rejection) for U.S. Appl. No. 18/836,215, filed Nov. 21, 2025.
Yeung et al., “RF safety of wires in interventional MRI: using a safety index”, Magnetic Resonance in Medicine: An Official Journal of the International Society for Magnetic Resonance in Medicine, (2002), vol. 47, No. 1, pp. 187-193.
Yun et al., “Breast Magnetic Resonance Imaging-Guided Biopsy”, The Korean Society of Radiology, (2016), 74(6), pp. 351-360.

* cited by examiner

MEDICAL DEVICES FOR INTERVENTIONAL MRI AND RELATED METHODS

CROSS REFERENCE TO RELATED APPLICATIONS

This application claims the benefit of U.S. Provisional Application No. 63/550,545 filed Feb. 6, 2024 entitled MEDICAL DEVICES FOR INTERVENTIONAL MRI AND RELATED METHODS, which is hereby incorporated by reference.

FIELD

The present disclosure relates generally to the field of medical devices. More particularly, the present disclosure relates to interventional medical devices useful in performing treatment under magnetic resonance imaging (MRI), methods of performing interventional medical treatment under MRI, and methods of making medical devices. Specific examples described herein relate to introducer sheaths.

BACKGROUND

Interventional procedures conducted under MRI have several benefits over X-Ray-guided interventions. For example, the patient is not exposed to ionizing radiation. Also, MRI provides the ability to characterize tissue and fluid flow during an interventional procedure. For at least these reasons, the use of interventional MRI is gaining wider acceptance and the number of procedures that can be performed under MRI is generally increasing.

The art provides only a limited number of interventional medical devices suitable for use under MRI, however, which continues to limit growth of the use of interventional MRI procedures. As a result, patients have not yet benefitted fully from interventional MRI technologies and, indeed, are often still limited to less convenient, and potentially less effective, options for certain treatments.

For example, without interventional MRI, addressing some conditions requires the use of multiple imaging modalities over the clinical path from initial testing to treatment. On a practical level, this use of multiple imaging modalities can require multiple patient visits to a healthcare facility. A conventional approach to the treatment of prostate cancer is illustrative—visualization, biopsy, and treatment are performed over the course of three separate patient visits. At a first visit, a scan is completed using a magnetic resonance scanner to produce an image showing the prostate and any abnormalities. The patient then leaves the facility and awaits a review of the image. If abnormalities exist, a second patient visit will occur such that a biopsy sample of the abnormal tissue can be completed. Software is used to merge magnetic resonance images with the procedural ultrasound to provide guidance in conducting the biopsy. This fusion decreases the value of the diagnostic magnetic resonance image. The patient then leaves the facility again and awaits a review of the biopsy sample to determine whether further treatment is required (e.g., if the review results in a positive prostate cancer diagnosis). If further treatment is required, the patient must visit the facility a third time for delivery of the treatment. Completion of these three patient visits often extends over months, prevents the patient from receiving rapid treatment, and increases the overall costs associated with treatment, both to the patient and to the healthcare providers involved. Furthermore, the use of software to merge images from multiple imaging modalities, such as magnetic resonance images and ultrasound images, has drawbacks, such as image overlay or alignment issues and the potential for compression shifting of tissues. Ultimately, these drawbacks of current treatment approaches can limit the overall effectiveness of the treatment. Interventional MRI has the potential to overcome these drawbacks.

Needs exist, therefore, for new and improved interventional medical devices useful in performing treatment under MRI, methods of performing interventional medical treatment under MRI, and methods of making medical devices.

BRIEF SUMMARY OF SELECTED EXAMPLES

Various example interventional medical devices useful in performing treatment under MRI, methods of performing interventional medical treatment under MRI, and methods of making medical devices are described herein.

One example medical device useful in performing treatment under MRI includes an elongate member having a proximal end, a distal end, and a circumferential wall having an outer surface and an inner surface that defines a lumen. The circumferential wall includes an inner tubular member formed of a first polymeric material and an outer tubular member formed of a second polymeric material. A reinforcement member is disposed within the circumferential wall between the inner tubular member and the outer tubular member and extends along a length of the elongate member. The reinforcement member is formed of a first material and having a first magnetic susceptibility. The medical device also includes a passive MRI marker attached to the elongate member and formed of a second material having a second magnetic susceptibility that is different than, and preferably greater than, the first magnetic susceptibility. In some aspects, the first material has a magnetic susceptibility not exceeding 3000 ppm. In some aspects, the second material has a magnetic susceptibility of at least about 7000 ppm. In some aspects, the first material comprises a paramagnetic material and the second material comprises a ferromagnetic material. In preferred forms, the medical device is an introducer sheath. In some aspects, the inner tubular member is formed of a lubricious fluoropolymer, the outer tubular member is formed of a thermoformable polymeric material that has been thermoformed against and around the reinforcement member and against an outer surface of the inner tubular member, the inner tubular member has a first longitudinal segment that longitudinally co-extends with the reinforcement member along the elongate member, the inner tubular member has a second longitudinal segment distal of a distal end of the reinforcement member, the second longitudinal segment having an outer surface, the elongate member includes a thermoformed polymeric material providing a distal tip of the elongate member extending distally beyond a distal end of the inner tubular member.

An example method for making a medical device useful in performing treatment under MRI includes positioning an elongate reinforcement member around an elongate polymeric inner tubular member, the reinforcement member being formed from a first material having a first magnetic susceptibility. The method further includes positioning an elongate thermoformable polymeric outer tubular member around the reinforcement member and inner tubular member, and thermoforming the outer tubular member against and around the reinforcement member and against an outer surface of the inner tubular member to provide an elongate reinforced tubular structure. The method further includes attaching a passive MRI marker formed from a second material to the reinforced tubular structure, the second material having a magnetic susceptibility that is different than, and preferably greater than, the first magnetic susceptibility. In some forms, the attaching includes positioning the passive MRI marker between the inner tubular member and the outer tubular member prior to the thermoforming. In other aspects, the attaching includes positioning the passive MRI marker in a hole in a thermoformed volume of polymeric material providing a distal tip of the elongate member.

Another example medical device comprises an elongate member having a proximal end, a distal end, and a circumferential wall having an outer surface and an inner surface that defines a lumen; a reinforcement member disposed within the circumferential wall, extending along a length of the elongate member and formed of a first material and having a first susceptibility; and a marker attached to the elongate member and formed of a second material and having a second susceptibility that is different from the first susceptibility.

Another example medical device comprises an elongate member having a proximal end, a distal end, and a circumferential wall having an outer surface and an inner surface that defines a lumen; a reinforcement member disposed within the circumferential wall, extending along a length of the elongate member, and formed of a first material having a first susceptibility; and a marker disposed within the circumferential wall distal to the reinforcement member and formed of a second material different from the first material and having a second susceptibility that is greater than the first susceptibility.

Another example medical device comprises an elongate member having a proximal end, a distal end, and a circumferential wall having an outer surface and an inner surface that defines a lumen; a reinforcement member comprising a coil disposed within the circumferential wall, extending along a length of the elongate member, and formed of a first material having a first susceptibility; and a marker disposed within the circumferential wall distal to the reinforcement member and formed of a second material different from the first material and having a second susceptibility that is greater than the first susceptibility.

Another example medical device comprises an elongate member having a proximal end, a distal end, and a circumferential wall having an outer surface and an inner surface that defines a lumen; a reinforcement member disposed within the circumferential wall, extending along a length of the elongate member and formed of a first material having a first magnetic susceptibility; and a marker attached to the elongate member and formed of a second material having a second magnetic susceptibility that is greater than the first magnetic susceptibility.

Another example medical device comprises an elongate member having a proximal end, a distal end, and a circumferential wall having an outer surface and an inner surface that defines a lumen; a reinforcement member disposed within the circumferential wall, extending along a length of the elongate member, and formed of a first material having a first magnetic susceptibility; and a marker disposed within the circumferential wall distal to the reinforcement member and formed of a second material different from the first material and having a second magnetic susceptibility that is greater than the first magnetic susceptibility.

Another example medical device comprises an elongate member having a proximal end, a distal end, and a circumferential wall having an outer surface and an inner surface that defines a lumen; a reinforcement member comprising a coil disposed within the circumferential wall, extending along a length of the elongate member, and formed of a first material having a first magnetic susceptibility; and a marker disposed within the circumferential wall distal to the reinforcement member and formed of a second material different from the first material and having a second magnetic susceptibility that is greater than the first magnetic susceptibility.

Another example medical device comprises an elongate member having a proximal end, a distal end, and a circumferential wall having an outer surface and an inner surface that defines a lumen; a reinforcement member comprising a mesh disposed within the circumferential wall, extending along a length of the elongate member, and formed of a first material having a first magnetic susceptibility; and a marker disposed within the circumferential wall distal to the reinforcement member and formed of a second material different from the first material and having a second magnetic susceptibility that is greater than the first magnetic susceptibility.

Various example methods of performing an interventional medical treatment under MRI are also included.

Various example methods of making a medical device are described.

Additional understanding of these and other example interventional medical devices, methods of performing interventional medical treatment under MRI, and methods of making a medical device can be obtained by review of the detailed description of selected examples, below, and the references drawings.

DETAILED DESCRIPTION OF SELECTED EXAMPLES

Figure 1:
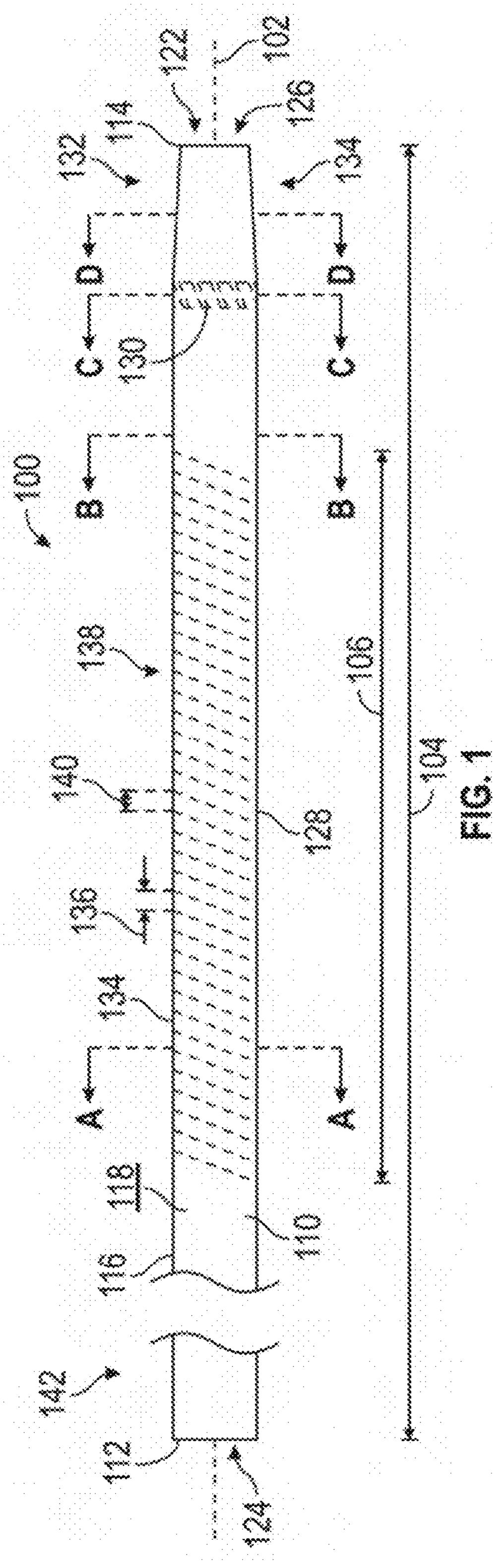
FIG. 1 is a side view of an example medical device.

The following detailed description and the appended drawings describe and illustrate various example interventional medical devices, imaging methods, methods of performing interventional medical treatment under MRI, and methods of making medical devices. The description and illustration of these examples are provided to enable one skilled in the art to make and use an interventional medical device and to perform imaging methods, methods of performing interventional medical treatment under MRI, and methods of making interventional medical devices. They are not intended to limit the scope of the invention, or its protection, in any manner. The invention is capable of being practiced or carried out in various ways and the examples described and illustrated herein are not considered exhaustive.

As used herein, the term "attached" refers to one member being secured to another member such that the members do not completely separate from each other during use performed in accordance with the intended use of an item that includes the members in their attached form.

As used herein, the term "circumference" refers to an external enclosing boundary of a body, element, or feature and does not impart any structural configuration on the body, element, or feature.

As used herein, the term "magnetic susceptibility" refers to the intrinsic property of a material that relates to how much the material will become magnetized in an applied magnetic field. When numeric values for magnetic susceptibility are provided herein, they refer to volume-based magnetic susceptibility in International System of Units (SI) values at 25° C. Some magnetic susceptibility values are given herein as parts per million ("ppm"), and persons skilled in the pertinent art will understand that the reference to "ppm" is equivalent to a reference to "$\times 10^{-6}$".

As used herein, the term "marker" refers to a discrete deposit of a first material on a second material such that the first material is visible under MRI and is distinguishable from the second material under MRI, a portion of an interventional device in which a first material has been incorporated into a second material such that the combination of the first and second materials is visible under MRI and is distinguishable from the second material under MRI, and a portion of an interventional device in which a material that forms a portion of an interventional device has been manipulated such that the portion is visible under MRI and is distinguishable from the remainder of the interventional device under MRI.

As used herein, the term "passive," in relation to a marker, refers to a marker that is either unpowered or powered exclusively by the electromagnetic field of a magnetic resonance scanner.

As used herein, the term "susceptibility," when not immediately preceded by "magnetic," refers to the ability of an element to influence an external magnetic field. Susceptibility is dependent on various properties of an element, including the size, density, geometric configuration, volume, and other physical properties of the element, and the magnetic susceptibility of the material of which the element is formed.

As used herein, the "maximum dimension" of a visible artifact refers to the maximum edge-to-edge distance of the visible artifact under MRI. Where a numeric value for the maximum dimension of a visible artifact is referenced or required to determine a feature disclosed herein, it is as determinable according to ASTM F2119-07 (2013) and using a primary field strength of 0.55 T and the following parameters:

| Gradient echo sequence | |
|---|---|
| Time to Echo (TE) [ms] | 15 |
| Repetition Time (TR) [ms] | 317 |
| Flip angle [°] | 30 |
| Matrix size | 256 × 256 |
| Slice thickness [mm] | 10 mm |
| Pixel bandwidth [Hz/px] | 120 |
| Field of View (FOV) [mm × mm] | 400 × 400 |

As used herein, the term "treatment" refers to a medical procedure performed on or in a portion of a body of a patient. Examples of treatments include delivery of an agent to a site within a body vessel, modification of a local environment inside of a body vessel such as by heating or cooling, and removal of a tissue or portion of a tissue from a site within a body of a patient (i.e., biopsy).

As used herein, the term "wire" refers to a strand or rod of material. The term does not require any particular cross-sectional shape, composition, physical properties, or production method by which a referenced element was made.

FIGS. 1, 2, 3, 4, 5, 6, and 7 illustrate an example medical device 100. The medical device 100 includes an elongate member 110 having a proximal end 112, a distal end 114, a lengthwise axis 102 extending between the proximal end 112 and the distal end 114, and a length 104 that extends from the proximal end 112 to the distal end 114. The elongate member 110 has a circumferential wall 116 having an outer surface 118 and an inner surface 120 that defines a lumen 122. The lumen 122 extends from a proximal opening 124 on the proximal end 112 to a distal opening 126 on the distal end 114. A reinforcement member 128 is disposed within the circumferential wall 116 and extends along a length 106 of the elongate member 110. The reinforcement member 128 is formed of a first material having a first susceptibility. A marker 130 is attached to the elongate member 110 and is formed of a second material having a second susceptibility that is different from the first susceptibility. The first and second materials can be the same or different. Thus, the first and second materials can have the same or different magnetic susceptibility.

In certain forms herein, the first material has a magnetic susceptibility not exceeding about 3000 ppm, or not exceeding about 2000 ppm, or not exceeding about 1000 ppm, and in some aspects in the range of about 1 ppm to about 3000 ppm or about 1 ppm to about 2000 ppm, or about 1 ppm to about 1000 ppm. Certain preferred first materials for these purposes include, as examples, titanium, tungsten, nickel-titanium alloys such as superelastic nickel-titanium alloys (e.g. nitinol), nickel-cobalt alloys such as superalloys containing nickel, cobalt, chromium and molybdenum (e.g. MP35N), and austentic nickel-chromium based superalloys (such as Inconel 625 or another Inconel alloy available from Special Metals Corporation).

As well, in certain forms, the second material, and any other material used herein to form a passive MRI marker, such as a metal, will have an absolute magnetic susceptibility value (positive or negative, i.e. including diamagnetic materials with a negative value and paramagnetic or ferromagnetic materials with a positive value) of at least about 10 ppm. In certain preferred forms, the second material, or any other material used herein to form a passive MRI marker, will have a magnetic susceptibility of at least about 500 ppm, or at least about 2000 ppm, or at least 7000 ppm, and typically in the range of about 500 ppm to about 1,000,000 and more preferably in the range of about 7000 ppm to about 100,000 (these values will be understood as positive values). In many forms, the second material will have a magnetic susceptibility that is greater than that of the first material. Preferred passive MRI marker-forming materials for these or other purposes herein include, for example: nickel, alloys of nickel, iron, alloys of iron, cobalt, alloys of cobalt, or other suitable metals. These may be selected to have magnetic susceptibility values as discussed herein and/or in some forms may be paramagnetic or ferromagnetic materials.

The elongate member 110 is formed of a polymeric material such that the reinforcement member 128 can be disposed within the circumferential wall 116 during fabrication. Any polymeric material can be used and a skilled artisan will be able to select a suitable polymeric material for the elongate member in a medical device according to a particular embodiment based on various considerations, including desired any desired handling and performance characteristics of the medical device, such as torqueability and pushability. Examples of suitable polymeric materials include, but are not limited to, heat-formable polymeric materials, such as polyamide materials. These polymeric materials are considered desirable at least because of their ability to melt and flow between and around elements during a heat forming or heat shrinking process. Nylon is considered particularly advantageous at least because of its ready availability and well-characterized nature.

The elongate member 110 can have any suitable form and a skilled artisan will be able to select a suitable form for a medical device according to a particular embodiment based on several considerations, including the intended use of the medical device and the nature of any body vessel within which the medical device is intended to be placed. In the illustrated example, the elongate member 110 includes a distal portion 132 that defines a taper 134 along the outer surface 118 such that the distal opening 126 has the same diameter as the diameter of the proximal opening 124. For example, the thickness of circumferential wall 116 can gradually become smaller over the distal portion 132 while the inner diameter of the lumen 122 is continuous over the distal portion 132. Alternatively, the elongate member 110 can include a distal portion 132 that defines a taper 134 along both the outer surface 118 and the inner surface 120 such that the distal opening 126 has a smaller diameter than the diameter of the proximal opening 124. Also alternatively, the elongate member 110 can have substantially continuous outer and inner diameters along its length.

The elongate member can have any suitable axial length and a skilled artisan will be able to select a suitable length for a medical device according to a particular embodiment based on various considerations, including the intended use of the medical device and the nature of any body vessel within which the medical device is intended to be placed. Examples of lengths considered suitable for a elongate member in a medical device according to the invention include, but are not limited to, lengths equal to, greater than, less than, or about 100 centimeters, 110 centimeters, 120 centimeters, 130 centimeters, 140 centimeters, 240 centimeters, 250 centimeters, 260 centimeters, 270 centimeters, 280 centimeters, between about 50 centimeters and about 350 centimeters, between about 100 centimeters and about 280 centimeters, between about 120 centimeters and about 260 centimeters, and any other length considered suitable for a medical device according to a particular embodiment.

Figure 2A:
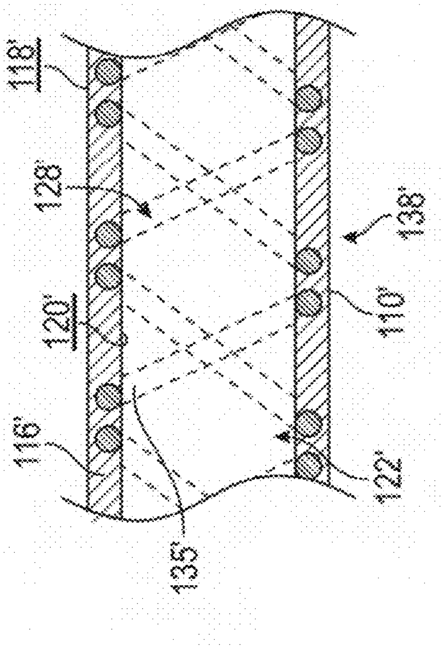
FIG. 2A is a magnified sectional view of an alternative medical device.
Figure 2:
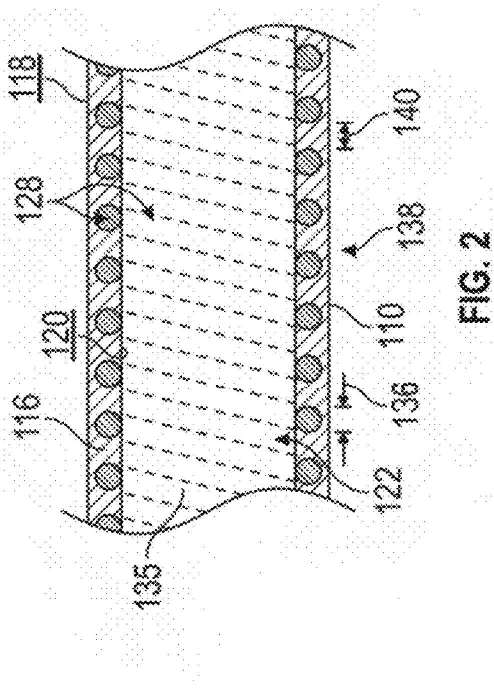
FIG. 2 is a magnified sectional view of the medical device illustrated in FIG. 1.
Figure 3:
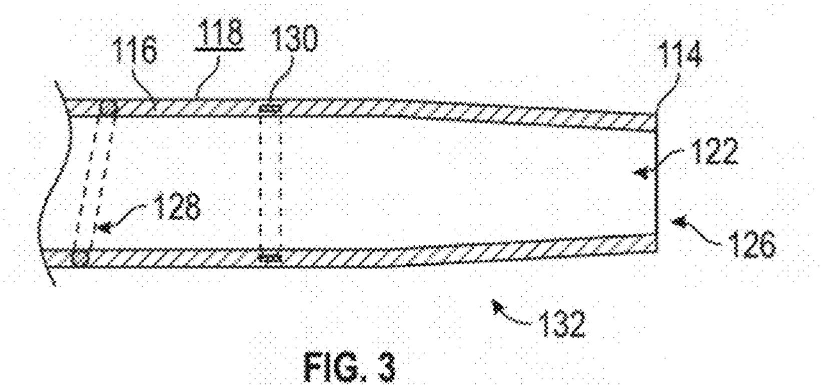
FIG. 3 is a magnified sectional view of the distal end of the medical device illustrated in FIG. 1.
Figure 4:
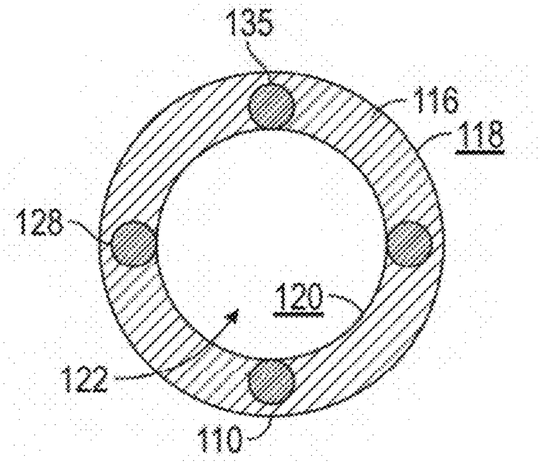
FIG. 4 is a sectional view of the tubular medical device illustrated in FIG. 1, taken along line A-A.
Figure 5:
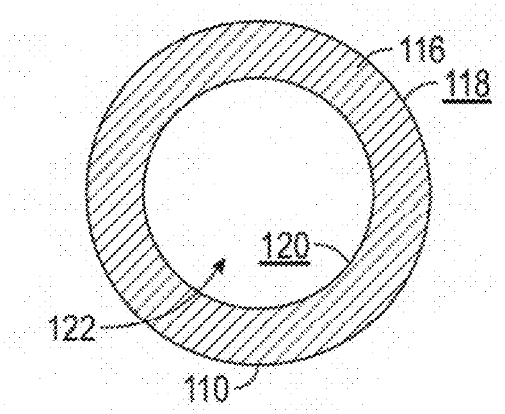
FIG. 5 is a sectional view of the tubular medical device illustrated in FIG. 1, taken along line B-B.

As best illustrated in FIGS. 2 and 4, reinforcement member 128 is embedded within the thickness of the circumferential wall 116 of the elongate member 110 such that the reinforcement member 128 is disposed entirely within the thickness of the elongate member 110 and such that no portion of the reinforcement member 128 breaches any portion of either the outer surface 118 or the inner surface 120 of the elongate member 110. The reinforcement member 128 extends around the lumen 122 and along an axial length 106 of the elongate member 110. The reinforcement member 128 is formed of a metal or an alloy and has a magnetic susceptibility that is less than the magnetic susceptibility of the marker 130.

The reinforcement member 128 can have any suitable structural configuration relative to the elongate member 110 that provides the desired extension around the lumen 122 and along an axial length 106 of the elongate member 110. A skilled artisan will be able to select a desirable structural configuration for the reinforcement member in a medical device according to a particular embodiment based on various considerations, including any desired handling characteristics of the medical device. In the illustrated embodiment, the reinforcement member 110 comprises a wire 135 having a thickness 136 and formed into a coil 138 extending around the lumen 122 and along an axial length 106 of the elongate member 110. Adjacent turns of the coil 138 are separated by a gap 140. The reinforcement member in a medical device according to a particular embodiment can have other another structural configuration, though. For example, the reinforcement member can form an interrupted coil, a coil having a variable pitch along its axial length, a coil having a variable diameter along its axial length, and combinations of these structural configurations. FIG. 2A illustrates an alternative elongate member 110' in which the reinforcement member 128' comprises a mesh 138' of wire members 135'. As with the embodiment illustrated in FIG. 2, the reinforcement member 128' is embedded within the thickness of the circumferential wall 116' such that the reinforcement member 128' is disposed entirely within the thickness of the elongate member 110', leaving no portion of the mesh 138' that breaches the outer surface 118' or the inner surface 120' of the elongate member 110'. Also similar to the embodiment illustrated in FIG. 2, the reinforcement member 128' extends around the lumen 122' of the elongate member 110'. Other examples of suitable structural configurations for the reinforcement member include, but are not limited to, a secondary structure that forms multiple cells, such as hexagon-shaped or octagon-shaped cells, or those in which a reinforcement member comprises a braided material that extends around a lumen of an elongate member (e.g., partially, entirely) and is embedded (e.g., entirely) within a thickness of a circumferential wall of the elongate member.

The reinforcement member 128 has a susceptibility that is different from the susceptibility of the marker 130. Accordingly, the reinforcement member 128 can be formed of any metal, alloy, or other material that provides the desired relative susceptibility as compared to the susceptibility of the marker 130. A skilled artisan will be able to select a suitable material for the reinforcement member in a medical device according to a particular embodiment based on various considerations, including the composition of the marker in the medical device. Suitable pairings of materials, properties, and structural configurations for the reinforcement member and the marker in medical devices according to the invention are described in detail below. Examples of suitable materials for the reinforcement member include, but are not limited to, Titanium, alloys, such as alloys containing less than or equal to 1% Iron by weight, such as Cobalt Chromium alloys, polymeric materials, such as polyether ether ketone (PEEK), and other materials.

The reinforcement member 128 can extend along any axial length of the elongate member 110 and a skilled artisan will be able to select a suitable axial length for a medical device according to a particular embodiment based on various considerations, including any desired handling characteristics of the medical device. As best illustrated in FIG. 1, the reinforcement member 128 in the example medical device 100 extends along an axial length 106 that is less than the total axial length 104 of the elongate member 110. A proximal portion 142 of the elongate member 110 includes the proximal end 112 and is free of the reinforcement member 128. That is, the reinforcement member 128 terminates and does not extend into the proximal portion 142 of the elongate member 110. Similarly, a distal portion 132 of the elongate member 110 includes the distal end 114 and is free of the reinforcement member 128. Thus, the reinforcement member 128 terminates and does not extend into the distal portion 132 of the elongate member 110. It is considered advantageous to axially separate the marker 130 from the distal end of the reinforcement member 128. This axial separation of these elements provides desirable imaging properties in light of the relative susceptibilities of the materials that form these elements, and also provides a desirable stiffness to the distal end relative to the portion of the elongate member that includes the reinforcement member without sacrificing the advantageous handling characteristics imparted onto other portions of the elongate member that include the reinforcement member. Thus, as best illustrated in FIG. 1, distal portion 132 of the elongate member 110 is free of the reinforcement member 128. Alternatively, however, a marker can be formed as a portion of a reinforcement member (e.g., attached to, formed from the same material) such that the material that forms the marker, or the portion of the material forming the marker, has a susceptibility that is different from the susceptibility of the material that forms the remainder of the reinforcement member, as described herein.

Examples of suitable axial lengths for a reinforcement member in a medical device according to a particular embodiment include, but are not limited to, 100% of the axial length of the elongate member of the medical device, about 100% of the axial length of the elongate member of the medical device, less than 100% of the axial length of the elongate member of the medical device, about 95% of the axial length of the elongate member of the medical device, about 90% of the axial length of the elongate member of the medical device, about 85% of the axial length of the elongate member of the medical device, and about 80% of the axial length of the elongate member of the medical device. Other examples of suitable axial lengths for a reinforcement member in a medical device according to a particular embodiment include, but are not limited to, between about 50% and about 100% of the axial length of the elongate member of the medical device, between about 60% and about 95% of the axial length of the elongate member of the medical device, between about 70% and about 95% of the axial length of the elongate member of the medical device, between about 80% and about 95% of the axial length of the elongate member of the medical device, and between about 90% and about 95% of the axial length of the elongate member of the medical device.

Figure 6:
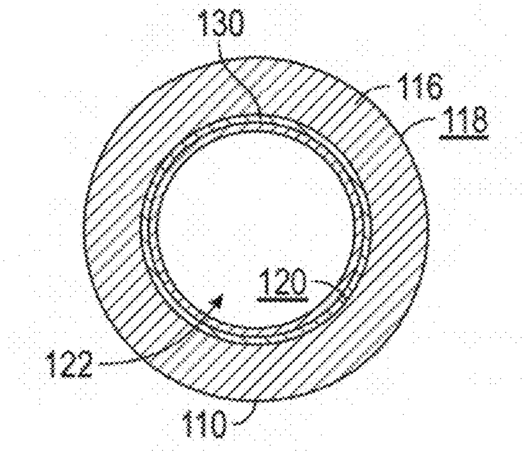
FIG. 6 is a sectional view of the tubular medical device illustrated in FIG. 1, taken along line C-C.
Figure 7:
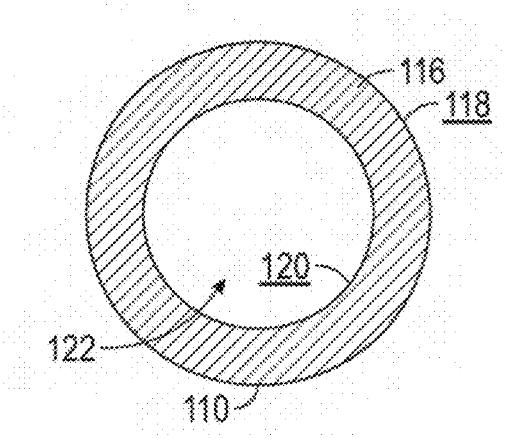
FIG. 7 is a sectional view of the tubular medical device illustrated in FIG. 1, taken along line D-D.

As best illustrated in FIGS. 1 and 6, marker 130 is embedded within the thickness of the circumferential wall 116 of the elongate member 110 such that the marker 130 is disposed entirely within the thickness of the elongate member 110 and such that no portion of the marker 130 breaches any portion of either the outer surface 118 or the inner surface 120 of the elongate member 110. In the illustrated embodiment, the marker 130 extends around the lumen 122 of the elongate member 110. Marker 130 is a passive marker and is formed of a metal or an alloy and has a susceptibility that is different from the susceptibility of the reinforcement member 128.

Marker 130 can have any structural configuration, and a skilled artisan will be able to select a suitable structural configuration for a medical device according to a particular embodiment based on various considerations, including any desired visualization characteristics when the medical device is used with imaging modalities, such as MRI. Examples of suitable configurations include, but are not limited to, a ring, a strip, a plug, a twisted band, a twisted ring, multiple bands attached to each other, multiple rings attached to each other, and other configurations. A circumferential band of material, as illustrated in FIGS. 1 and 6, is considered particularly advantageous. A medical device can include any number of markers, too, and a skilled artisan will be able to select a suitable number of markers for a medical device according to a particular embodiment based on various considerations, including any desired visualization patterns when the medical device is used with imaging modalities, such as MRJ. Examples of suitable numbers include, but are not limited to, one, more than 1, two, a plurality, three, more than three, four, five, six, seven, eight, nine, ten, and more than ten.

The marker 130 can be disposed at any suitable position relative to reinforcement member 128, and a skilled artisan will be able to select a suitable position for a marker relative to the reinforcement member in a medical device according to a particular embodiment based on various considerations, including any desired visualization patterns when the medical device is used with imaging modalities, such as MRJ. As best illustrated in FIG. 1, the marker 130 in the example medical device 100 is positioned distal to the reinforcement member 128, in the distal portion 132 of the elongate member 110. Other examples of suitable positions include, but are not limited to, within an axial portion of the elongate member that includes the reinforcement member such that the marker overlaps the reinforcement member, within an axial portion of the elongate member that is proximal to the reinforcement member, at the distal end of the elongate member, at the proximal end of the elongate member, and combinations of these positions with multiple markers.

The marker 130 has a susceptibility that is different from the magnetic susceptibility of the reinforcement member 128. Accordingly, the marker can be formed of any metal, alloy, or other material that provides the desired relative susceptibility as compared to the susceptibility of the reinforcement member 128. A skilled artisan will be able to select a suitable material for the marker in a medical device according to a particular embodiment based on various considerations, including the composition of the reinforcement member in the medical device. Suitable pairings of materials for the reinforcement member and the marker in medical devices according to the invention are described in detail below. Examples of suitable materials for the marker include, but are not limited to, metals, such as Titanium, Nickel, and other metals, alloys, such as stainless steel alloys, including 304V stainless steel and 316LVM stainless steel, ferromagnetic materials, paramagnetic materials, alloys containing at least 50% Iron by weight, ferromagnetic and paramagnetic compounds, such as those in powder form, Tantalum powder, Barium Sulfate, Bismuth Oxychloride, Tungsten, Iron Oxide nanoparticles, functionalized magnetite, Gadolinium, Ferritic Stainless Steel, Ferritic Stainless Steel powders, 316 Stainless Steel, nylon compounded with another material, such as tungsten, bismuth, and others, and any other material considered suitable for a particular embodiment. Alternative to incorporating a marker into the circumferential wall of an elongate member of a medical device, alternative embodiments can include a marker disposed on a surface of the elongate member, such as an inner or outer surface. For example, a marker can be printed onto or adhered to an inner or outer surface of an elongate member of a medical device. For example, an ink containing a material having a magnetic susceptibility that is greater than the magnetic susceptibility of the reinforcement member in a medical device, such as an ink containing magnetic particles, an ink containing Iron Oxide nanoparticles, or an ink containing Iron Oxide nanoparticles bound to phospholipids, can be printed onto an outer surface and/or an inner surface of an elongate member to form a marker in a medical device according to an embodiment. A marker can be disposed on a surface by other suitable processes, too, such as chemical vapor deposition. Also alternatively, a tape including a material having a magnetic susceptibility that is greater than the magnetic susceptibility of the reinforcement member in a medical device, such as magnetic tape, can be adhered to an outer surface or an inner surface of an elongate member to form a marker in a medical device according to an embodiment. Selection of a marker, or markers, to include in a medical device according to a particular embodiment can also be based upon the field strength, or field strengths, within which the medical device is intended to be used. For example, a medical device that includes a marker can be utilized to complete one, or more than one, interventional procedure under MRI utilizing one or more field strengths (0.55 T, 1.5 T, or 3.0 T). Material or materials can be selected for a marker or markers in a medical device according to an embodiment based on these expected field strengths and the expected visual artifacts produced by a marker or markers formed of a particular material and having a particular structural configuration.

The reinforcement member in medical devices according to the invention has a susceptibility that is different from the susceptibility of a marker in the medical device. Thus, the marker in medical devices according to the invention has a susceptibility that is different from the susceptibility of the reinforcement in the medical device. Any pairing of materials for these elements that provides this relative relationship of the susceptibilities for these elements, which is considered critical to the performance of medical devices according to the invention, can be used in a medical device according to a particular embodiment. Indeed, the reinforcement member and the marker can be formed of the same or different materials as long as the relative relationship of the susceptibilities for these elements is provided. In some embodiments, different materials having different magnetic susceptibilities are used for the reinforcement member and the marker. In these embodiments, the reinforcement member and the marker have different susceptibilities and are formed of materials having different magnetic susceptibilities. For these embodiments, a skilled artisan will be able to select a material for one of these elements in a medical device according to a particular embodiment based on various considerations, including the composition of the other of these elements and any desired performance characteristics or imaging characteristics for the medical device. Examples of suitable pairings of different materials for the reinforcement member and the marker include, but are not limited to, a first material for the reinforcement member and a second, different material for the marker, such as a paramagnetic material for the reinforcement member and a ferromagnetic material for the marker, an alloy containing less than or equal to 1% Iron by weight for the reinforcement member and an alloy containing at least 50% Iron by weight for the marker, a Cobalt Chromium alloy for the reinforcement member and a stainless steel for the marker, and a Nickel Cobalt alloy (e.g. containing Nickel, Cobalt, Chromium and Molybdenum), such as MP35N, or tungsten, for the reinforcement member and a stainless steel, such as 304V stainless steel of 316LVM stainless steel, for the marker. In other embodiments, the reinforcement member and the marker are formed of the same material. In these embodiments, while the reinforcement member and the marker have different susceptibilities, the reinforcement member and the marker have the same magnetic susceptibility. For example, in the illustrated embodiment, the reinforcement member 128 and the marker 130 can be formed of the same material, giving the reinforcement member 128 and the marker 130 the same magnetic susceptibility. To provide the different susceptibilities for these elements 128, 130, one can be work-hardened or manipulated in some manner that provides a susceptibility that is different from the susceptibility of the other.

Examples of suitable materials for the reinforcement member include, but are not limited to, metals, such as Titanium, alloys, such as stainless steel, Nickel-containing alloys, Cobalt-containing alloys, alloys containing less than or equal to 1% Iron by weight, such as Cobalt Chromium alloys, tungsten, polymeric materials, such as polyether ether ketone (PEEK), glass fibers, and the like.

The medical device 100 can include additional optional components. For example, a liner, such as a liner formed of a lubricious fluoropolymer, such as polytetrafluoroethylene (PTFE), can be disposed on the inner surface 120 of the circumferential wall. Also, a handle, connector, or other component can be attached to the proximal end 112 of the elongate member 110 to aid in handling of the medical device 100 during use or to facilitate use of the medical device 100 with other medical devices, such as catheters and the like.

Figure 8:
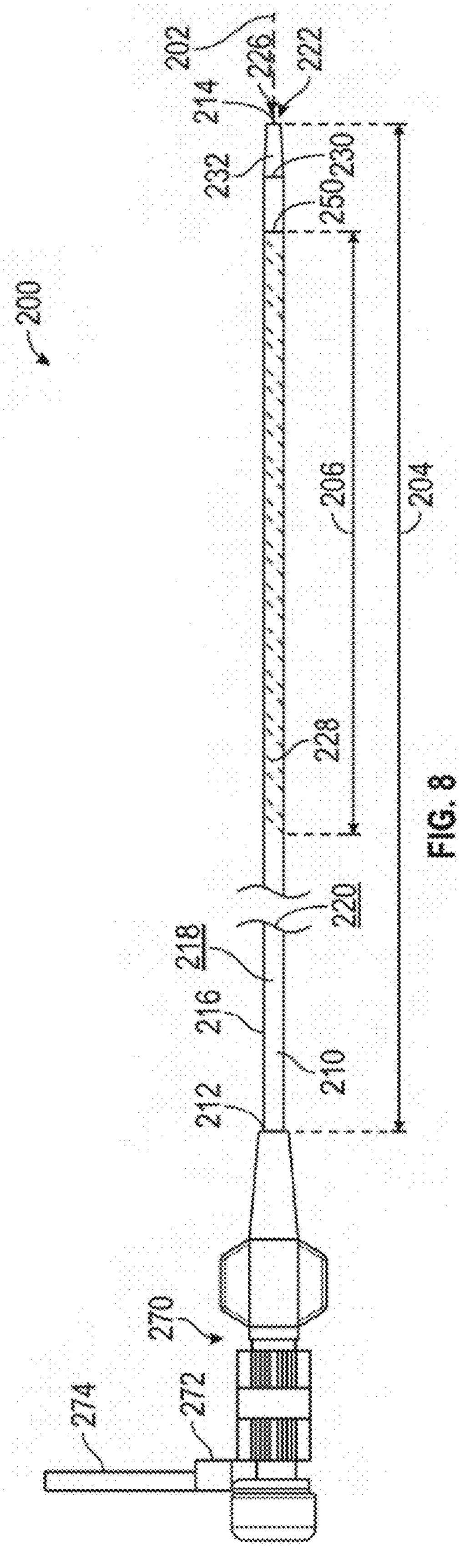
FIG. 8 is a side view of an example introducer sheath.

Medical devices according to the invention can take various configurations, depending on the intended use of the particular medical device. The medical device illustrated in FIGS. 1, 2, 3, 4, 5, 6, and 7 is one example configuration. FIG. 8 illustrates another example medical device 200. The medical device 200 is an introducer sheath useful in the placement, delivery, or deployment of another interventional medical device, such as a catheter, a stent, a stent graft, a valve, a filter, a coil, an embolization device, such as a bead or beads or a particle or particles, or the like, in a body vessel of an animal, such as a human. The medical device 200 is similar to the medical device 100 described above, except as detailed below. Thus, medical device 200 includes an elongate member 210 having a proximal end 212, a distal end 214, a lengthwise axis 202 extending between the proximal end 212 and the distal end 214, and a length 204 that extends from the proximal end 212 to the distal end 214. The elongate member 210 has a circumferential wall 216 having an outer surface 218 and an inner surface 220 that defines a lumen 222. The lumen 222 extends from a proximal opening (not illustrated in the Figure) on the proximal end 212 to a distal opening 226 on the distal end 214. A reinforcement member 228 is disposed within the circumferential wall 216 and extends along a length 206 of the elongate member 210. The reinforcement member 228 is formed of a first material having a first susceptibility. A first marker 230 is attached to the elongate member 210 and is formed of a second material having a second susceptibility. A second marker 234 is attached to the elongate member 210 and is formed of a third material having a third susceptibility. The first, second, and third materials can be the same or different. The second and third susceptibilities can be the same or different, but each is different from the first susceptibility. A dilator having a tapered distal end can be disposed longitudinally through the lumen 222 of the elongate member 210 for accessing and dilating a vascular access site, e.g., over a conventional wire guide (not shown).

In this example, a connector hub 236 is attached about the proximal end 212 of the elongate member 210. Connector hub 236 may include an elastomeric seal member, such as a conventional silicone disk 237 (illustrated in phantom in the Figure), for preventing backflow of fluids through the connector hub 236 during use of the medical device 200. The elastomeric seal member has an opening through which another device, such as a dilator, can be passed, wherein the seal member seals against the outer surface of the other device to prevent backflow of fluids. The seal member can also have a closed condition when there is no device received therethrough, for preventing backflow in that state as well. Connector hub 236 also includes a side arm 238, to which a polymeric tube 240 and other components, such as a Luer lock connector, may be connected for introducing and aspirating fluids therethrough in conventional fashion.

In this example, medical device 200 includes a first marker 230 and a second marker 234. Each of the first marker 230 and the second marker 234 is disposed distal to the reinforcement member 228. This positioning of multiple markers, each of which has a susceptibility that is different from the susceptibility of the reinforcement member 228, is considered advantageous at least because it positions the markers in a location on the axial length of the medical device 200 that is ultimately positioned at or near a point of treatment in a body vessel during use of the medical device 200 and distal to the reinforcement member. When used with imaging modalities, such as MRI, this positioning, along with the relative susceptibilities, provides desirable imaging artifacts than can be used for confirmation of placement of the distal portion 232 of the medical device 200.

Figure 9:
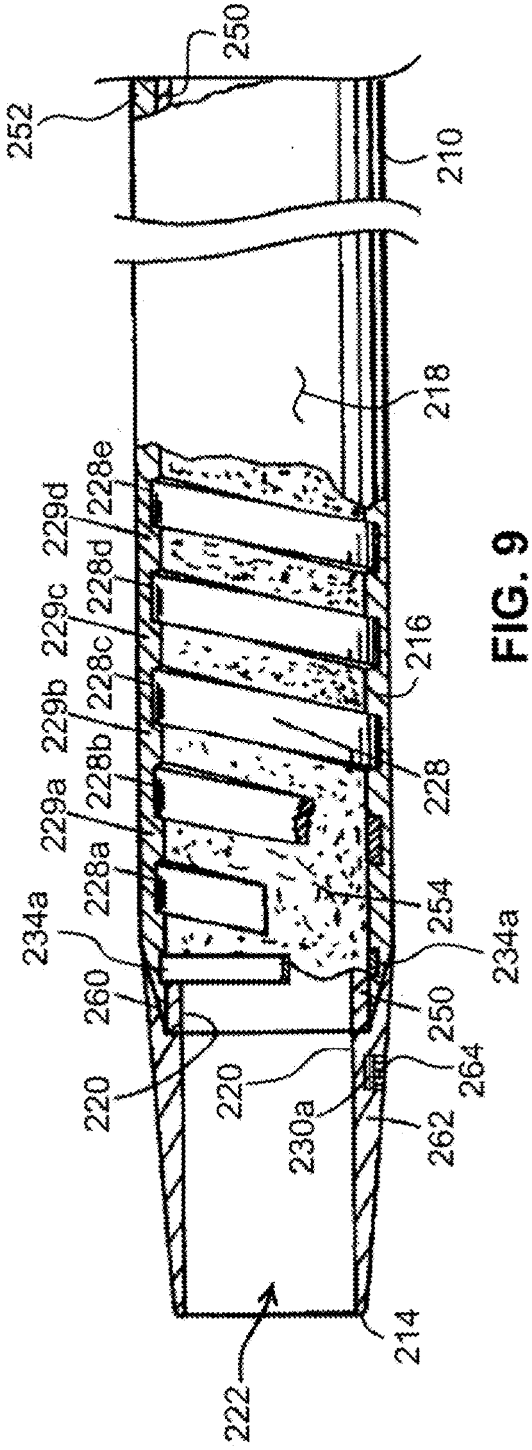
FIG. 9 is a side view of another example introducer sheath.

FIG. 9 depicts a partially sectioned view of the distal region of another embodiment of a medical device 200A, in the form of an introducer sheath. Medical device 200A is similar to medical device 200 described above, except as detailed below. Thus, medical device 200A includes an elongate member 210 having a proximal end, a distal end 214, a lengthwise axis extending between the proximal end and the distal end 214. The elongate member 210 has a circumferential wall 216 having an outer surface 218 and an inner surface 220 that defines a lumen 222. The lumen 222 extends from a proximal opening (not illustrated in FIG. 9) on the proximal end to the distal opening 226 on the distal end 214. A reinforcement member 228 is disposed within the circumferential wall 216. The reinforcement member 228 is formed of a first material having a first susceptibility. A first marker 230*a* is attached to the elongate member 210 and is formed of a second material having a second susceptibility. A second marker 234*a* is attached to the elongate member 210 and is formed of a third material having a third susceptibility. The first, second, and third materials can be the same or different. The second and third susceptibilities can be the same or different, but each is different from the first susceptibility.

In this example, medical device 200A includes a first marker 230*a* and a second marker 234*a*. Each of the first marker 230*a* and the second marker 234*a* is disposed distal to the reinforcement member 228.

The medical device 200A includes inner tube 250, the reinforcement member 228 in the form of a flat wire coil compression fitted around the inner tube 250, and an outer tube 252 mechanically connected to outer surface 254, which can be a roughened outer surface, of the inner tube through the spacings of the flat wire coil. Inner tube 250 is preferably a lubricous polymeric material tube such as polytetrafluoroethylene having a uniform inside diameter, for example in the range of about 2 mm to about 2.25 mm, and for example having a wall thickness in the range of about 0.025 mm to about 0.05 mm. The inner tube 250 preferably has a minimum inside dimension of about 2 mm after the heating as described below. The lubricous polytetrafluoroethylene or other polymeric material presents a slippery inner surface 256 for the easy insertion and withdrawal of medical devices such as dilators or catheters. Outer surface 254 of the inner tube 250 can be chemically etched or otherwise treated to form a rough outer surface to which outer tube 252 is mechanically connected, for instance using a heat shrinking and formation process as described below. In preferred forms, the uniform inner diameter of inner tube 250 extends to the proximal end opening of the medical device 200A. The wall of the inner tube 250 prevents the turns of compression-fitted reinforcement member 228 (preferably a flat wire coil as illustrated) from protruding into the lumen 222 of medical device 200A.

The flat wire of the a coil providing reinforcement member 228, in preferred forms, will have a thickness (which becomes disposed in the radial direction) in the range of about 0.03 mm to about 0.15 mm and a width in the range of about 0.25 mm to about 0.5 mm. The flat wire is preferably formed of a metal, and more preferably a metal having a magnetic susceptibility not exceeding about 3000 ppm, or not exceeding about 2000 ppm, or not exceeding about 1000 ppm, and in some forms in the range of about 1 ppm to about 3000 ppm, in the range of about 1 ppm to about 2000 ppm, or in the range of about 1 ppm to about 1000 ppm. Preferred materials for forming the flat wire include those disclosed herein for forming the reinforcement member of the medical device.

The flat wire coil providing reinforcement member 228 includes a plurality of flat wire turns, for example, 228*a*-

228*e*, with spaces 229*a*-229*e* therebetween, which can in some forms be of equal longitudinal width to one another. The flat wire coil providing reinforcement member 228 is preferably formed from a flat rectangular wire of the first material, for example wound with a space in the range of about 0.125 mm to about 0.4 mm, desirably uniform, between the flat wire turns of the coil. The flat wire coil is compression fitted around the outer surface of inner tube 250, for example about 3 mm to about 10 mm (e.g. 4 mm) from the distal end thereof and about 3 mm to about 10 mm (e.g. 5 mm) from the proximal end thereof. The coil can be compression fitted over the inner tube 250 by collapsing inner tube 250 and positioning the coil thereover. The second material of the passive MRI marker 234*a* can also be provided over the inner tube 250. For example, in some forms the marker 234*a* can be a discrete, solid band of the second material that is fitted, e.g. compression fitted, over the inner tube 250. In other forms, the second material of the marker 234*a* can be deposited and held upon (for example attached to) the outer surface 254 of the inner tube 250. For example, the second material of the marker can be in the form of particles, and a flowable composition containing the particles dispersed in a matrix-forming material can be applied to the outer surface 254 and then cured to form a solid matrix, in the form of a band or other layer, adhered to the outer surface 254 and containing the particles. The flowable composition can be configured to cure in any suitable fashion, including for example by solvent evaporation and/or chemical crosslinking. In some forms, the solid matrix will be a thermoformable solid matrix, for example comprised of a thermoformable polymer and the particles. Potential MRI-artifact-generating particulate materials for the second material include as examples particles of a material that has a magnetic susceptibility greater than about 500 ppm, and preferably greater than about 2000 ppm. Examples of MRI-artifact-generating particles include particles of nickel, a nickel alloy, iron, an iron alloy, iron oxide, or titanium.

Inner tube 250 can then be expanded with compressed air to engage and compression fit to the inner surface of the flat wire coil (and in some forms the inner surface of a fitted solid band of the second material providing marker 234*a*). A mandrel inserted through the passageway of the inner tube 250 can be used to further compress the inner tube 250 against the coil turns (and the inner surface of the fitted solid band of the second material when used) during the manufacture of the sheath as hereinafter described. The coil is positioned away from the distal and proximal ends of the inner tube to permit tapering and flaring of the sheath without extending the coil turns through the material, for example polyamide material, of the outer tube 252.

The outer tube 252 can be made of a heat formable material, such as a heat formable polyamide material (e.g. nylon). The outer tube 252 can be heat shrunk over the second material providing marker 234*a* and over the coil providing reinforcement member 228, which in turn is compression fitted over inner tube 250. The wall thickness of the outer tube is preferably in the range of about 0.15 to about 0.3 mm, or about 0.15 to about 0.2 mm (e.g. about 1.65 mm). In manufacture, the outer tube 252 can be heated and compressed against and around the reinforcement member 228, e.g. through the spaces between the coil turns, with a heat shrink tube, and also against the outer surface 254 of the inner tube 250, which can connect the outer tube 252 to the outer surface 254 of the inner tube 250. A reinforced elongate tubular structure is thereby formed. The outside diameter of the outer tube 252 can be about 0.45 mm to about 0.65 mm, or about 0.5 mm to about 0.6 mm (e.g. about 0.55 mm) greater than that of the inner tube 250. In a further step during manufacture, after the outer tube 252 is heat shrunk onto the surface of the inner tube 250, the shrink tube is removed therefrom. A taper can thereafter be formed at the distal end of the medical device 200A to provide tapered distal end 258 thereof. In some forms, the wall thickness of the elongate member 210 including the inner tube 250, the reinforcement member 228, and the outer tube 250 is about 0.25 mm to about 0.35 mm.

In some methods of manufacture, the distal ends of the inner and outer tubes 250 and 252 can be cut, for example, to within about 0.25 mm to about 2.5 mm from the end of the flat wire coil. The remaining length of outer tube 252 that extends distal of the flat wire coil is externally tapered about the distal end to form contact surface area 260. Tapered distal end 258 can be formed by cutting and slitting a length (e.g. about 3 mm) of heat formable (e.g. polyamide) tubing and inserting it into a taper mold as is known. The length of tubing in the mold is heated, and the distal end of the elongate member 16 including the inner tube 250, the reinforcement member 228, and the outer tube 252, with a mandrel inserted therethrough, is inserted into the taper mold to thermally bond the heat formable (e.g. polyamide) tip material 262 to the outer tube 252 and to form tapered distal end 258, as shown. In other methods of manufacture, a distal region of the outer tube 252 extending beyond the distal end of the inner tube 250 can be thermoformed in a mold to provide the distal tip material 262 of the distal end 258. The distal end 214 of the device is typically positioned a first distance of about 2 to about 4 mm (e.g. approximately 3 mm) beyond the distal end of the inner tube 250 and about 1.1 to about 1.5 times such first distance beyond the distal end of the reinforcement member 228.

The illustrated medical device 200A also includes passive MRI marker 230*a*, which in the illustrated form is disposed in the tip material 262. Marker 230*a* can be in the form of a discrete volume of the second material, e.g. a plug. In providing marker 230*a*, a hole 264 can be created in the tip material 262 and the plug of the second material inserted into the hole and potentially positionally secured with an adhesive.

Plug marker 230*a* includes a material having a magnetic susceptibility suitable for generating the visible artifact under MRI as discussed herein (herein sometimes called a "passive MRI marker-forming material"). It has been found that relatively small amounts of suitable materials can be used for these markers. In certain forms, a plug marker or markers described herein will be formed of a passive MRI marker-forming material, such as a metal, having an absolute magnetic susceptibility value (positive or negative) of at least about 10 ppm. In certain preferred forms, the passive MRI marker-forming material for the plug marker(s) will have a magnetic susceptibility of at least about 500 ppm, or at least about 2000 ppm, or at least 7000 ppm, and typically in the range of about 500 ppm to about 1,000,000 and more preferably in the range of about 7000 ppm to about 100,000 (these values will be understood as positive values). In some forms, the marker-forming material will have a volume not exceeding 5 $mm^3$, or not exceeding 3 $mm^3$, or not exceeding 1 $mm^3$, or not exceeding 0.1 $mm^3$; in each of these aspects, the volume may be at least 0.00005 $mm^3$, or at least about 0.0001 $mm^3$. In more preferred forms where a relatively high magnetic susceptibility material is used, for example a magnetic susceptibility of at least about 1 (nickel, for example, as a magnetic susceptibility of about 1.1), a volume of the passive MRI marker-forming material not exceeding 0.1 $mm^3$, for example in the range of 0.00001 $mm^3$ to 0.1 $mm^3$, or in the range of 0.00005 $mm^3$ to 0.02 $mm^3$, can be used in forming the passive MRI marker 230*a*. Particular materials that may be used are discussed elsewhere herein. It will be understood that generally the higher the magnetic susceptibility exhibited by an MRI marker-forming material, the lower the volume of that material that will be needed to form a visible artifact of a given size. These aspects can be selected and controlled by persons of skill in the art to provide passive MRI markers configured to generate visible artifacts of a size, or relative size, as discussed herein. The ability to utilize relatively small volumes of passive MRI marker-forming material and yet generate beneficially sized visible artifacts is advantageous, as it enables the incorporation of a marker while maintaining the physical size and performance properties of the medical device.

Figure 10:
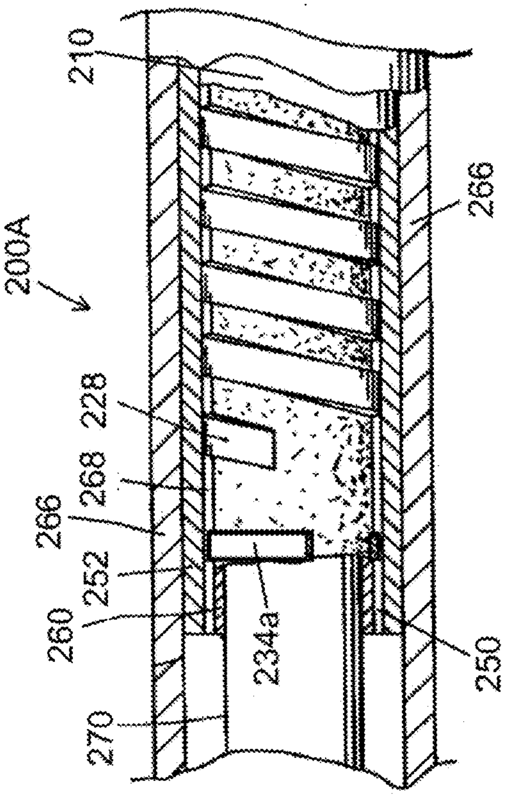
FIG. 10 is a side view illustrating a stage in the manufacture of the example introducer sheath of FIG. 9.
Figure 11:
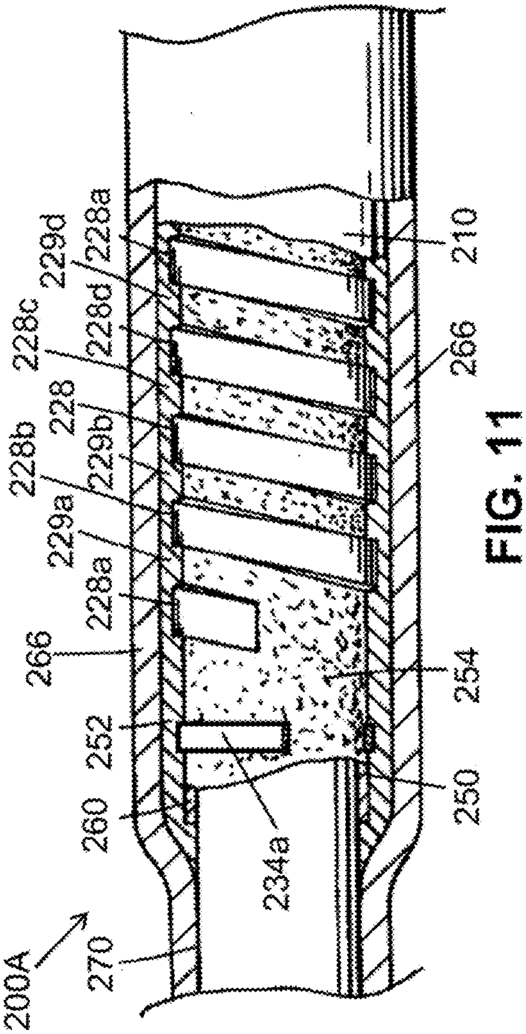
FIG. 11 is a side view illustrating another stage in the manufacture of the example introducer sheath of FIG. 9.

Reference will now be made to FIGS. 10 and 11 to described certain methods that can be used in making medical devices herein. FIG. 10 depicts a partially sectioned view of an assembly used to make medical device 200A, with a heat shrink tube 266 positioned over outer tube 252, reinforcement member 228, and marker 234*a* with longitudinal space 268 therebetween. As previously described, the flat wire coil providing reinforcement member 228 is compression fitted around inner tube 250 and the second material of the marker 234*a* is positioned on or over the inner tube 250. Prior to heating shrink tube 266 and forming outer tube 252, mandrel 270 is inserted through lumen 222. The heat shrink tube 266 can, for example, be a fluorinated ethylene propylene heat formable material.

FIG. 11 depicts heat shrink tube 266 being heated to cause shrinkage thereof. As the heat shrink tube 266 shrinks, the material of the heated outer tube 252 is compressed between the coil turns, e.g. coil turns 228*a*-228*e* in spaces 229*a*-229*d*, and against and around marker 234*a*, to mechanically connect with the outer surface 254 of the inner tube 250. The heat formable outer tube 252 can also be self-leveling to provide a uniform outer diameter surface for the elongate member 210 of the medical device 200A. Heat shrink tube 266 can then be split from the elongate member 210. As previously described, a tapered distal end 258 can then be formed. Also, when included, the marker 230*a* can then be incorporated into the tip material 262 of the tapered distal end 258.

Figure 12:
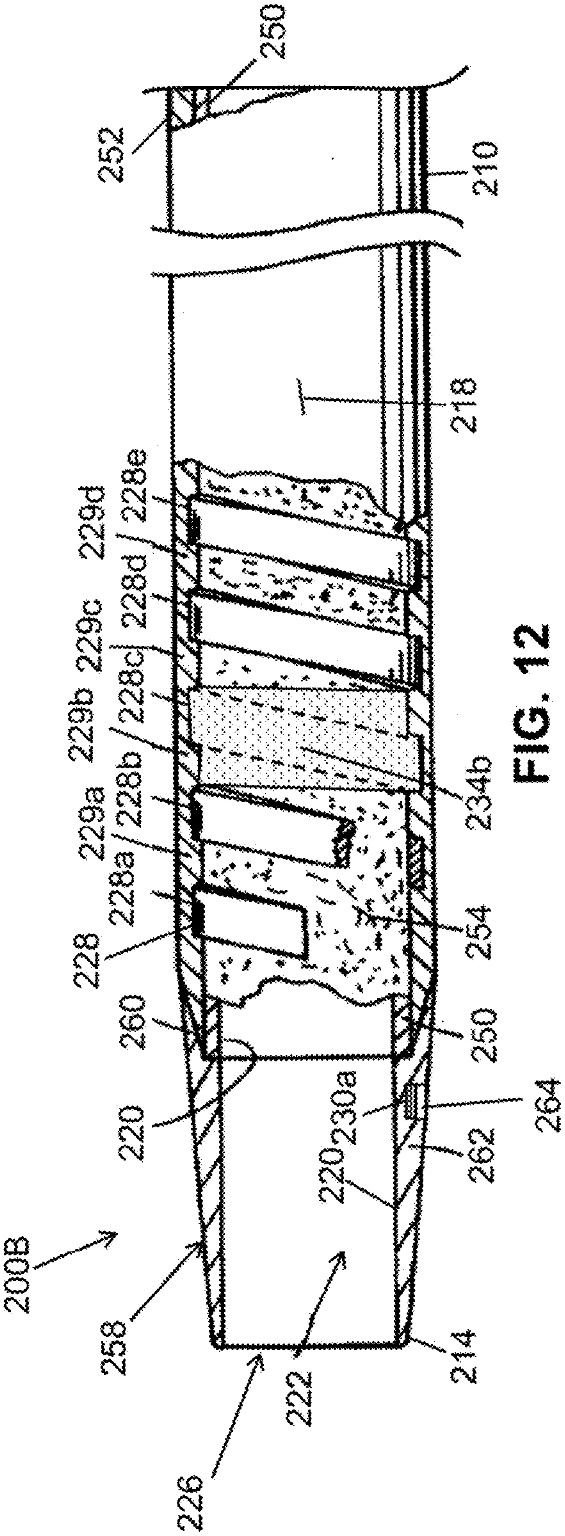
FIG. 12 is a side view of another example introducer sheath.

FIG. 12 depicts a partially sectioned view of the distal region of another embodiment of a medical device 200B, in the form of an introducer sheath. Medical device 200*b* is similar to medical device 200A described above, except as detailed below. In this example, medical device 200B includes the first marker 230*a* distal to the reinforcement member 228 (e.g. embedded within the tip material 262 as shown) and a second marker 234*b* at a position longitudinally coinciding with a segment of the reinforcement member 228. While only one such marker longitudinally coinciding with a segment of reinforcement member 228 is shown, it will be understood that a plurality of such markers, for example from two to about ten such markers, longitudinally spaced from one another along the length of elongate member 210, can be included in medical device 200B.

As in device 200A discussed above, the flat wire coil providing reinforcement member 228 includes a plurality of flat wire turns, for example, 228*a*-228*e*, with spaces 229*a*-229*e* therebetween. The flat wire coil is compression fitted around the outer surface of inner tube 250. The second material of the passive MRI marker 234*b* can also be provided positioned over the reinforcement member 228 and the inner tube 250. For example, in some forms the marker 234*b* can be a circumferential band layer or other layer of a malleable film or foil containing the second material that is positioned over the reinforcement member 228 and inner tube 250. In other forms, the second material of the marker 234*b* can be deposited and held upon (for example attached to) the outer surface of the reinforcement member and in some forms both the outer surface of the reinforcement member 228 and the outer surface 254 of the inner tube 250. For example, the second material of the marker can be in the form of particles. For instance, a flowable composition containing the particles dispersed in a matrix-forming material can be applied to (e.g. sprayed or printed or otherwise deposited upon) the outer surface 254 and then cured to form a solid matrix, in the form of a band or other layer, adhered to the outer surface of the reinforcement member 228, or to the outer surface of both the reinforcement member 228 and the outer surface 254 of the inner tube 250, and containing the particles. The flowable composition can be configured to cure in any suitable fashion, including for example by solvent evaporation and/or chemical crosslinking. In some forms, the solid matrix will be a thermoformable solid matrix, for example comprised of a thermoformable polymer and the particles. In still other manufacturing methods, the particles of the second material can be loose particles (i.e. not dispersed in a liquid carrier) and can be held, e.g. magnetically, in the desired location during thermoforming of the outer tube 252 to fix their position. Inner tube 250 can then be expanded with compressed air to engage and compression fit to the inner surface of the flat wire coil. A mandrel inserted through the passageway of the inner tube 250 can be used to further compress the inner tube 250 against the coil turns during the manufacture of the medical device as described hereinabove.

The outer tube 252 can be heat shrunk over the second material providing marker 234*b* and over the coil providing reinforcement member 228, which in turn is compression fitted over inner tube 250. In manufacture, the outer tube 252 can be heated and compressed through the spaces between the coil turns with a heat shrink tube for mechanically connecting to outer surface 254 of the inner tube 250 and engaging the reinforcement member 228 and the second material of the marker 234*b*. A taper can thereafter be formed at the distal end of the medical device 200B to provide tapered distal end 258 thereof and, when present, the marker 230*a* can be incorporated in the distal tip material 262.

Figure 13:
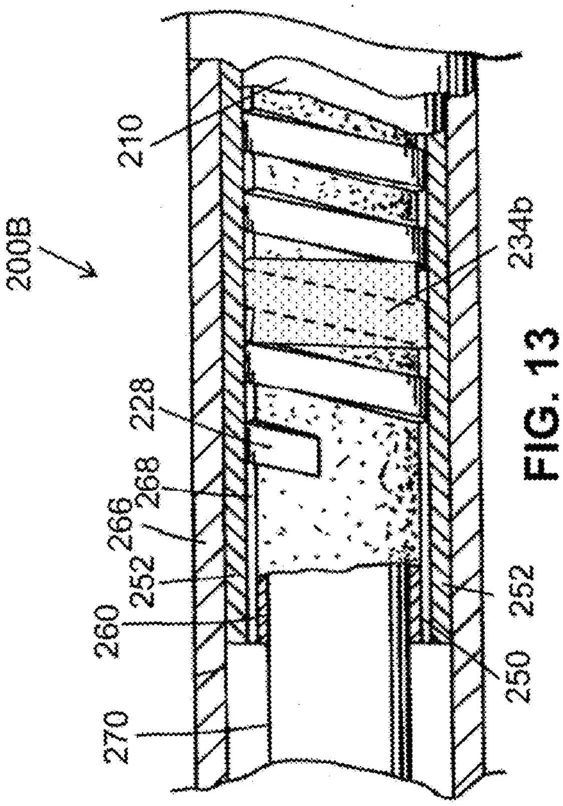
FIG. 13 is a side view illustrating a stage in the manufacture of the example introducer sheath of FIG. 12.
Figure 14:
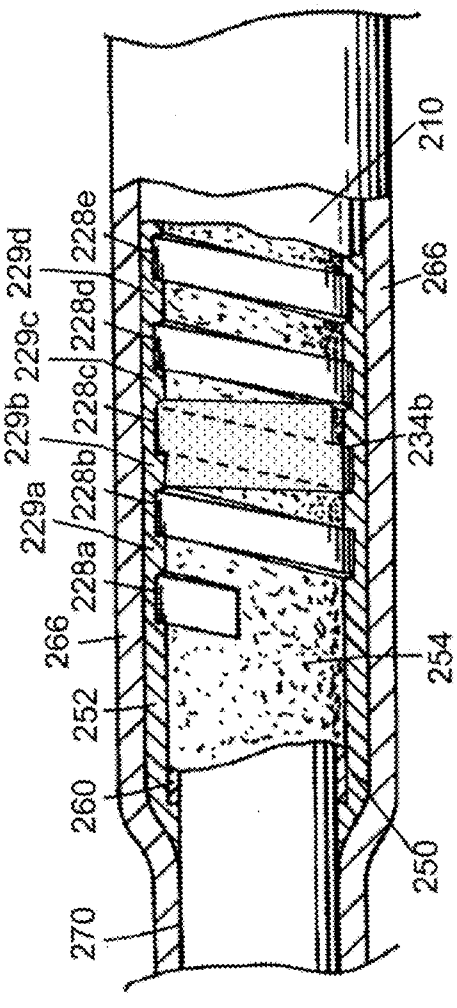
FIG. 14 is a side view illustrating another stage in the manufacture of the example introducer sheath of FIG. 12.

Reference will now be made to FIGS. 13 and 14 to described certain methods that can be used in making medical devices herein. FIG. 13 depicts a partially sectioned view of an assembly used to make medical device 200B, with a heat shrink tube 266 positioned over outer tube 252, reinforcement member 228, and marker 234*a* with longitudinal space 268 therebetween. Prior to heating shrink tube 266 and forming outer tube 252, mandrel 270 is inserted through lumen 222.

FIG. 14 depicts heat shrink tube 266 being heated to cause shrinkage thereof. As the heat shrink tube 266 shrinks, the material of the heated outer tube 252 is compressed between the coil turns, e.g. coil turns 228*a*-228*e* in spaces 229*a*-229*d*, and against marker 234*b*, and to mechanically connect with the outer surface 254 of the inner tube 250.

Figure 15:
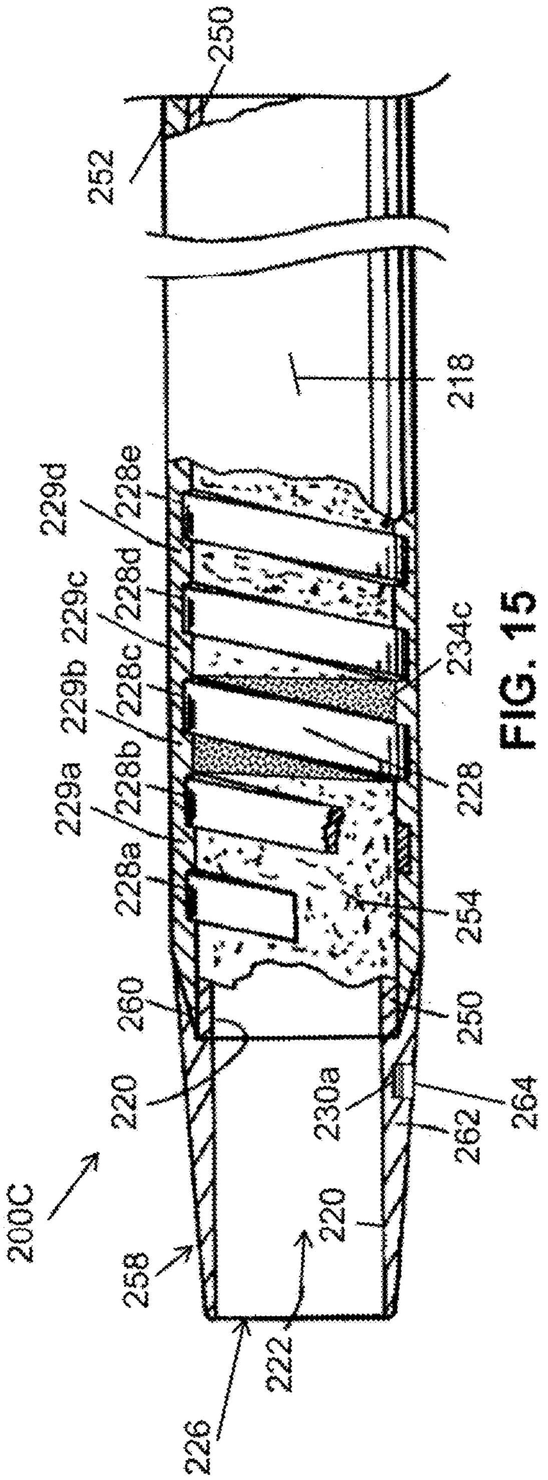
FIG. 15 is a side view of another example introducer sheath.

FIG. 15 depicts a partially sectioned view of the distal region of another embodiment of a medical device 200C, in the form of an introducer sheath. Medical device 200C is similar to medical device 200A described above, except as detailed below. In this example, medical device 200C includes the first marker 230*a* distal to the reinforcement member 228 (e.g. embedded within the tip material 262 as shown) and a second marker 234*c* at a position longitudinally coinciding with a segment of the reinforcement member 228. While only one such marker longitudinally coinciding with a segment of reinforcement member 228 is shown, it will be understood that a plurality of such markers, for example from two to about ten such markers, longitudinally spaced from one another along the length of elongate member 210, can be included in medical device 200B.

As in device 200A discussed above, the flat wire coil providing reinforcement member 228 includes a plurality of flat wire turns, for example, 228*a*-228*e*, with spaces 229*a*-229*e* therebetween. The flat wire coil is compression fitted around the outer surface of inner tube 250. The second material of the passive MRI marker 234*c* can also be provided positioned between the reinforcement member 228 and the inner tube 250. For example, in some forms the marker 234*c* can be a circumferential band layer or other layer of a malleable film or foil containing the second material that is positioned between the reinforcement member 228 and inner tube 250 for example provided on or over the outer surface 254 before fitting the reinforcement member 228 around the inner tube 250. In other forms, the second material of the marker 234*c* can be deposited and held upon (for example attached to) the outer surface outer surface 254 of the inner tube 250. For example, the second material of the marker can be in the form of particles, and a flowable composition containing the particles dispersed in a matrix-forming material can be applied to (e.g. sprayed or printed or otherwise deposited upon) the outer surface 254 and then cured to form a solid matrix, in the form of a band or other layer, adhered to the outer surface 254 of the inner tube 250, and containing the particles. The flowable composition can be configured to cure in any suitable fashion, including for example by solvent evaporation and/or chemical crosslinking. In some forms, the solid matrix will be a thermoformable solid matrix, for example comprised of a thermoformable polymer and the particles. In some forms, the second material of the marker 234 can be located between turns of the reinforcement member 228. For example, the marker 234 can be a solid continuous volume of the second material, such as a plug, ribbon or wire, positioned to occur between turns of the reinforcement member 228. Where such a volume of the second material is an elongate member, such as an elongate wire or ribbon, the elongate member can be wound circumferentially around the outer surface 254 of the inner tube 250 so that it does or will occur within the spaces between turns of the reinforcement member 258. Before or after positioning of the second material of the marker 234*c*, the reinforcement member 228 can be fitted around the inner tube 250. Inner tube 250 can be expanded with compressed air to engage and compression fit to the inner surface of the flat wire coil providing the reinforcement member 228. A mandrel inserted through the passageway of the inner tube 250 can be used to further compress the inner tube 250 against the coil turns during the manufacture of the medical device as described hereinabove.

The outer tube 252 can be heat shrunk over the coil providing reinforcement member 228, which in turn is compression fitted over inner tube 250. In manufacture, the outer tube 252 can be heated and compressed through the spaces between the coil turns with a heat shrink tube for mechanically connecting to outer surface 254 of the inner tube 250 and engaging the reinforcement member 228 and the second material of the marker 234*c*. A taper can thereafter be formed at the distal end of the medical device 200B to provide tapered distal end 258 thereof and, when present, the marker 230*a* can be incorporated in the distal tip material 262.

Figure 16:
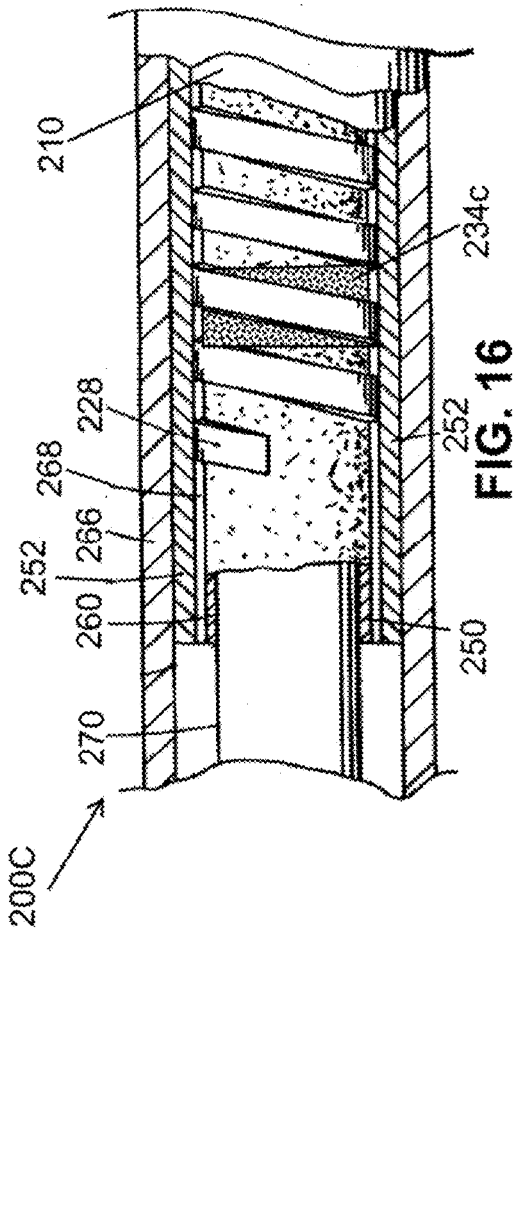
FIG. 16 is a side view illustrating a stage in the manufacture of the example introducer sheath of FIG. 15.
Figure 17:
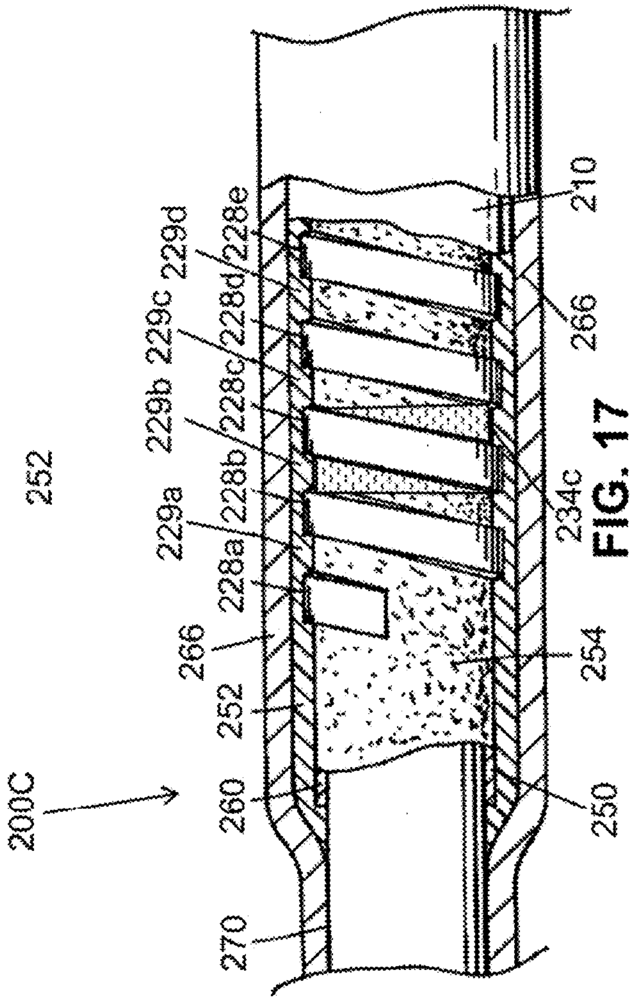
FIG. 17 is a side view illustrating another stage in the manufacture of the example introducer sheath of FIG. 15.

Reference will now be made to FIGS. 16 and 17 to further described certain methods that can be used in making medical devices herein. FIG. 16 depicts a partially sectioned view of an assembly used to make medical device 200C, with a heat shrink tube 266 positioned over outer tube 252, marker 234*c*, and reinforcement member 228, with longitudinal space 268 therebetween. Prior to heating shrink tube 266 and forming outer tube 252, mandrel 270 is inserted through lumen 222.

FIG. 17 depicts heat shrink tube 266 being heated to cause shrinkage thereof. As the heat shrink tube 266 shrinks, the material of the heated outer tube 252 is compressed between the coil turns, e.g. coil turns 228*a*-228*e* in spaces 229*a*-229*d*, and against at least portions of marker 234*c* (e.g. portions occurring in spaces between turns of the coil), and to mechanically connect with the outer surface 254 of the inner tube 250.

Advantageously, the circumferential band or other layer-form marker(s), such as markers 234*a*, 234*b* and 234*c* discussed above, can occur within a relatively small region of the elongate member 210. For example, such markers can occur within a longitudinal length not exceeding 10 mm, or not exceeding 5 mm, and typically in the range of 0.2 to 5 mm. As well, relatively thin layer thicknesses have been found to be effective for generating visible artifacts. The band or other layer preferably has a thickness not exceeding about 0.1 mm, and can be in the range of about 0.00025 mm to about 0.02 mm, or about 0.001 mm to about 0.015 mm, or about 0.0025 to about 0.015 mm; and/or can include a volume of the passive MRI marker-forming second material not exceeding 0.02 $mm^3$, or not exceeding 0.015 $mm^3$, or in the range of about $4\times10^{-5}$ $mm^3$ to about 0.02 $mm^3$; Passive MRI markers provided in such limited regions can facilitate avoidance or minimization of any impact of the marker(s) on the dimensions or performance properties of the elongate member 210.

In advantageous forms, the passive MRI markers disclosed herein will be configured to generate a visible artifact having a maximum dimension that is at least about 1.2 times the diameter of the longitudinal segment of the elongate member 210 on which they occur, typically in the range of about 1.2 times to about 50 times, and more typically in the range of about 2 to about 30 times, and even more typically in the range of about 3 to about 20 times. In addition or alternatively, such a maximum dimension of the visible artifact can be in the range of about 0.5 to about 3 cm, or about 1 to about 2 cm. The selection of the second material and the volume of the second material incorporated in the passive MRI marker(s) can be controlled to provide these visible artifact sizes.

EXAMPLES

Figure 18:
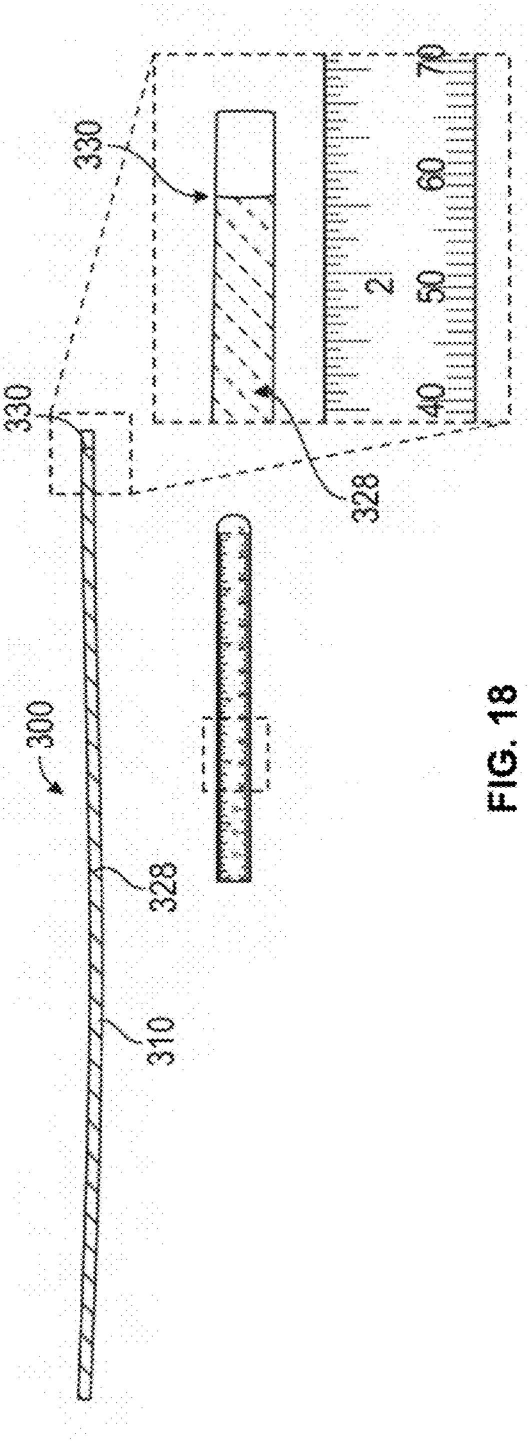
FIG. 18 is a side view of another example medical device, including a magnified view of the distal portion of the medical device.

FIG. 18 illustrates an example medical device 300 that includes an elongate member 310, a reinforcement member 328 comprising a coil formed of MP35N Nickel Cobalt, and a marker 330 disposed distal to the reinforcement member 328 and comprising a circumferential ring of 304V stainless steel. The coil was made from flat wire MP35N having a thickness of approximately 0.1 mm and a width of approximately 0.3 mm. The MP35N material had a magnetic susceptibility of approximately 900 ppm.

Figure 19:
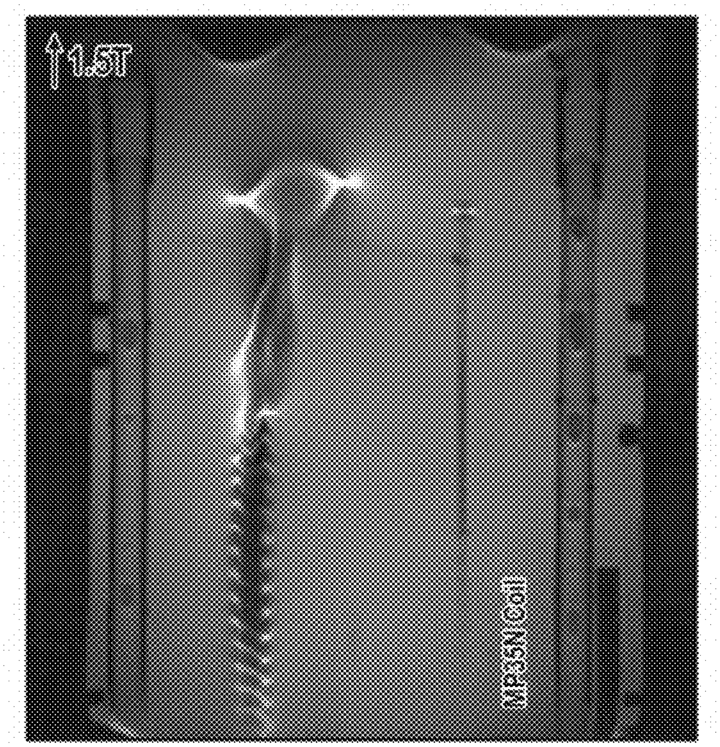
FIG. 19 is a magnetic resonance image of a prior art medical device and a medical device according to an embodiment.
Figure 20:
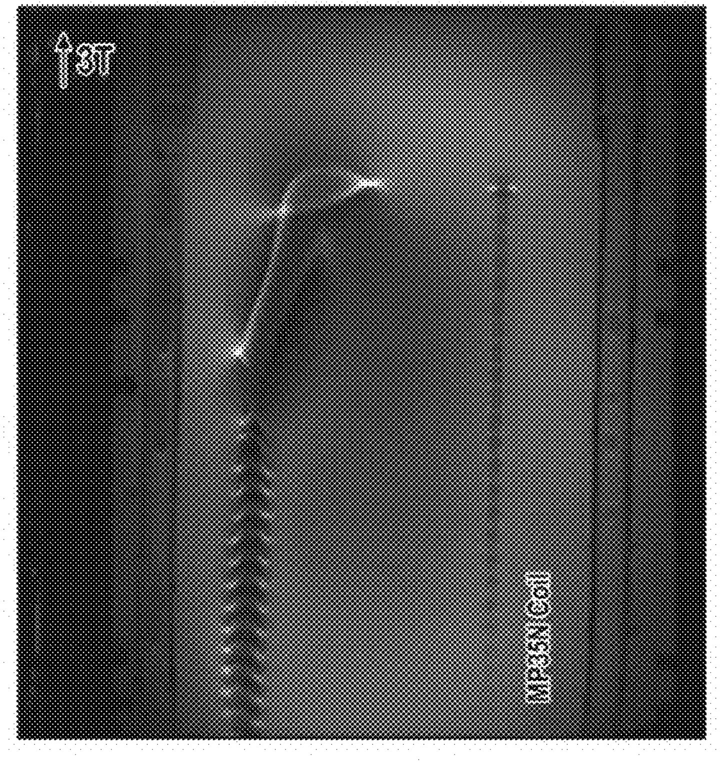
FIG. 20 is a magnetic resonance image of a prior art medical device and a medical device according to an embodiment.

Each of FIG. 19 and FIG. 20 illustrates artifacts in a magnetic resonance image from a prior art medical device having a reinforcement member comprising a stainless steel coil (left side in both Figures) and the medical device 300 illustrated in FIG. 18 (right side in both Figures). FIG. 19 is an image taken under a spin echo imaging sequence at 1.5 T in copper sulfate as a phantom solution. FIG. 20 is an image taken under a spin echo imaging sequence at 3 T in copper sulfate as a phantom solution.

Figure 21:
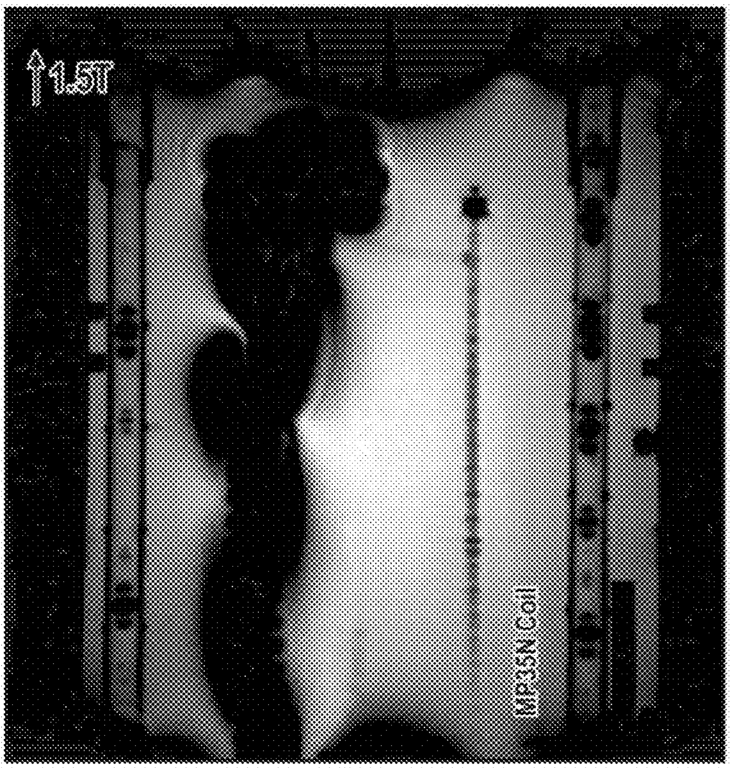
FIG. 21 is a magnetic resonance image of a prior art medical device and a medical device according to an embodiment.
Figure 22:
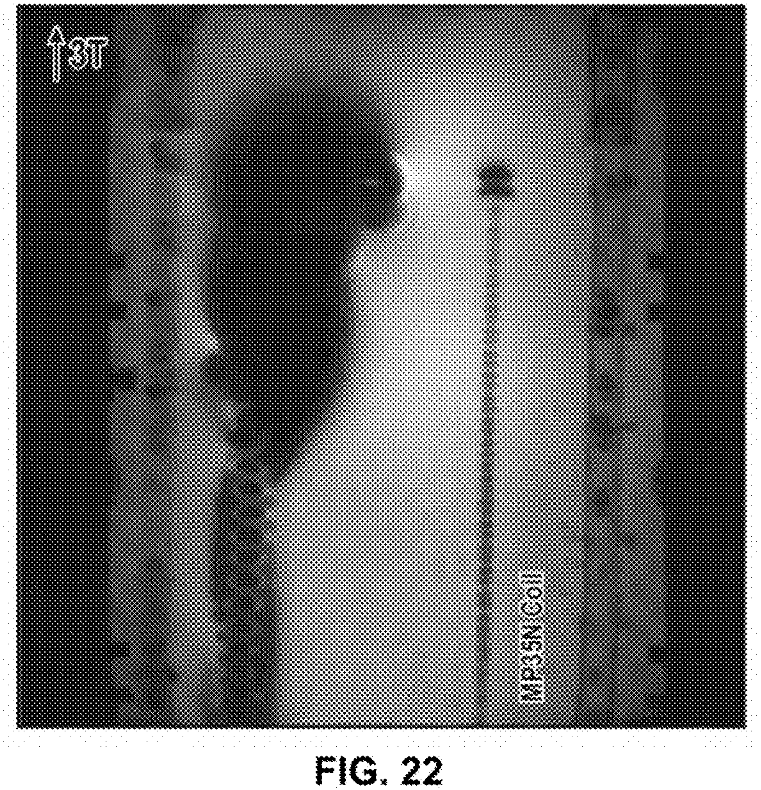
FIG. 22 is a magnetic resonance image of a prior art medical device and a medical device according to an embodiment.

Each of FIG. 21 and FIG. 22 illustrates artifacts in a magnetic resonance image from a prior art medical device having a reinforcement member comprising a stainless steel coil (left side in both Figures) and the medical device 300 illustrated in FIG. 9 (right side in both Figures). FIG. 21 is an image taken under a gradient refocusing echo (GRE) imaging sequence at 1.5 T in copper sulfate as a phantom solution. FIG. 22 is an image taken under a gradient refocusing echo (GRE) imaging sequence at 3 T in copper sulfate as a phantom solution.

Figure 23:
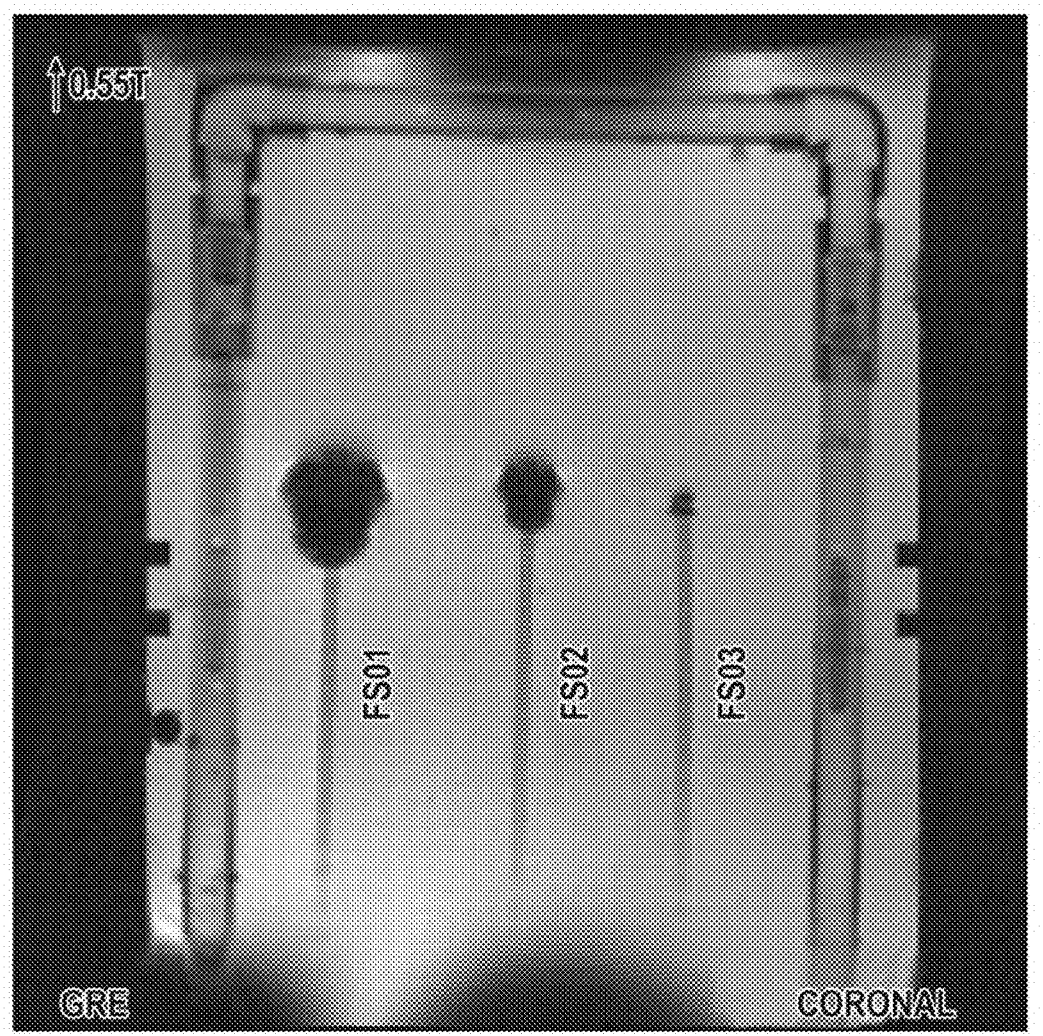
FIG. 23 is a magnetic resonance image of three medical devices according to embodiments.

FIG. 23 illustrates artifacts in a magnetic resonance image from first, second, and third example medical devices according to embodiments of the invention. The first example medical device comprises a coil formed of MP35N Nickel Cobalt and a single marker disposed distal to the reinforcement member and comprising a circumferential band of 304V stainless steel. The second example medical device comprises a coil formed of MP35N Nickel Cobalt and a single marker disposed distal to the reinforcement member and comprising a twisted circumferential band of 304V stainless steel. The third example medical device comprises a coil formed of MP35N Nickel Cobalt and a single marker disposed distal to the reinforcement member and comprising a circumferential band of 316LVM stainless steel.

Figure 24:
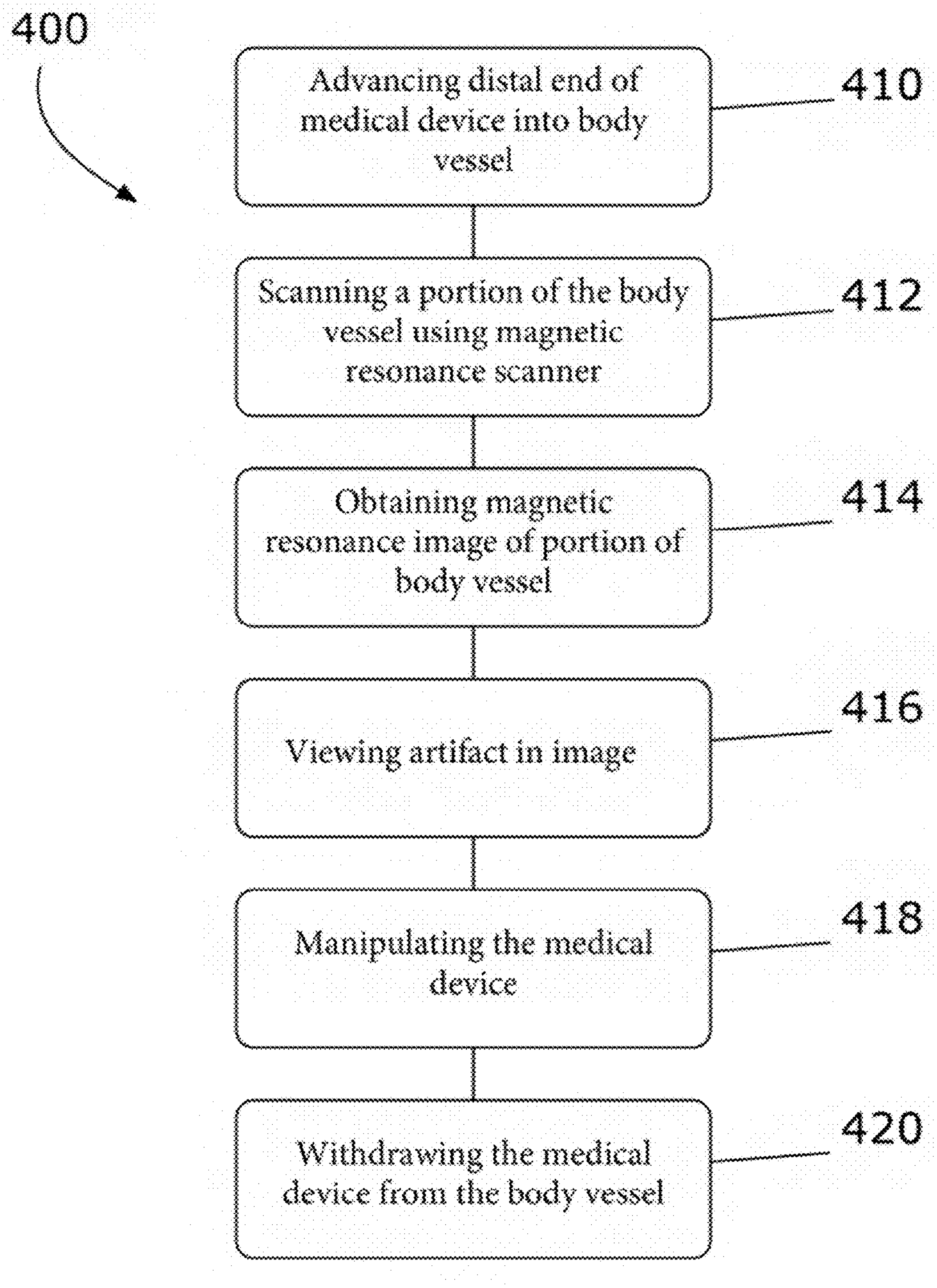
FIG. 24 is a flowchart illustration of an example method of performing an interventional medical treatment.

FIG. 24 is a schematic illustration of an example method 400 of performing an interventional medical treatment under MRI.

An initial step 410 comprises advancing the distal end of a medical device to a first location within a body vessel of an animal, such as a human and until a marker of the medical device is disposed at a second location within the body vessel. Another step 412 comprises scanning a portion of the body vessel that includes the second location within the body vessel using a magnetic resonance scanner. Another step 414 comprises obtaining a magnetic resonance image of the portion of the body vessel such that the image includes an artifact indicative of the presence of the marker within the portion of the body vessel. Another step 416 comprises viewing the artifact in the image generated by the presence of the marker. Another step 418 comprises manipulating the medical device based on the location of the artifact relative to the body vessel. Another step 420 comprises withdrawing the medical device from the body vessel.

The step 410 of advancing the distal end of a medical device is performed using a medical device according to an embodiment of the invention, such as any of the example medical devices described herein. Thus, the medical device includes an elongate member defining a lumen, a reinforcement member disposed within a circumferential wall of the elongate member and comprising a metal or alloy having a first magnetic susceptibility, and at least one marker disposed within or otherwise attached to the circumferential wall of the elongate member and comprising a metal or alloy having a second magnetic susceptibility that is greater than the first magnetic susceptibility.

Step 412 can be accomplished by scanning the portion of the body vessel using a magnetic resonance scanner having any suitable number and type of magnetic resonance image parameters, such as gradient refocusing echo imaging, spin echo imaging, true fast imaging with steady-state precession, fast low flip angle shot spoiled gradient-echo imaging, field strengths, such as 0.55 T, 1.5 T, 3 T, between about 0.055 T and 1.5 T, and fields less than 1 T, slice thickness, flip angle, field-of-view, resolution, gradient fields, and any other image parameter considered suitable for a particular embodiment.

Step 414 can be accomplished by obtaining the magnetic resonance image from the magnetic resonance scanner used in step 412.

Step 416 can be accomplished by reviewing the magnetic resonance image obtained in step 414 and identifying an artifact in the image based on the presence of the marker in the medical device.

Step 418 is performed in a manner that achieves, or that contributes to the achievement of, a desired clinical outcome of the method 400 of performing an interventional medical treatment. As such, the nature of the step 418 of manipulating the medical device will depend on the nature of the medical device and the desired clinical outcome. Examples of suitable actions that can be performed for this step include, but are not limited to, axially advancing the medical device within the bodily passage, rotating the medical device within the bodily passage, advancing another medical device through the lumen of the elongate member of the medical device, deploying another medical device from a position within the lumen of the elongate member of the medical device, and axially withdrawing a portion of the medical device to allow another medical device or a portion of another medical device to radially expand within the body vessel. In alternative embodiments, step 418 can be omitted from method 400 when manipulation of the interventional medical device is not desired.

The step 420 of withdrawing the medical device from the body vessel is performed by axially retracting the medical device from the body vessel until the distal end of the medical device is no longer disposed within the body vessel.

Any of the steps being performed by a magnetic resonance scanning can be accomplished using any suitable magnetic resonance scanner, such as conventional magnetic resonance scanners, magnetic resonance scanners that utilize 0.55 T fields, 1.5 T fields, 3 T fields, fields between about 0.055 T and 1.5 T, fields less than 1 T, and any other magnetic resonance scanner considered suitable for a particular embodiment.

A method of making a medical device includes disposing a reinforcement member formed of a first material and having a first susceptibility within a circumferential wall of an elongate member and attaching a marker formed of a second material and having a second susceptibility that is different from the first susceptibility to the circumferential wall of the elongate member. The first material and the second material can be the same or different. Thus, the first material and the second material can have the same or different magnetic susceptibilities. In one example method, the first and second materials are the same and an additional step of work hardening the marker is included to provide the different susceptibilities for the marker and the reinforcement member.

LISTING OF CERTAIN DISCLOSED EMBODIMENTS

The following provides an enumerated listing of some Embodiments disclosed herein. It will be understood that this listing is illustrative and non-limiting, and that additional embodiments will be understood by skilled persons to have been disclosed herein, including but not limited to additional embodiments in which one, two, or more, features disclosed hereinabove is/are combined with the features of the enumerated Embodiments below.

Embodiment 1. A medical device, comprising:

an elongate member having a proximal end, a distal end, and a circumferential wall having an outer surface and an inner surface that defines a lumen, wherein the circumferential wall includes an inner tubular member formed of a first polymeric material and an outer tubular member formed of a second polymeric material;

a reinforcement member disposed within the circumferential wall between the inner tubular member and the outer tubular member, extending along a length of the elongate member, and formed of a first material and having a first magnetic susceptibility; and a passive MRI marker attached to the elongate member and formed of a second material having a second magnetic susceptibility that is different than, preferably greater than, the first magnetic susceptibility.

Embodiment 2. The medical device of Embodiment 1, wherein the first material has a magnetic susceptibility not exceeding 3000 ppm, or not exceeding about 2000 ppm, or not exceeding about 1000 ppm.

Embodiment 3. The medical device of Embodiment 1 or 2, wherein the second material has a magnetic susceptibility of at least about 500 ppm, or at least about 2000 ppm, or at least about 7000 ppm, or in the range of about 500 ppm to about 1,000,000, or in the range of about 7000 ppm to about 100,000.

Embodiment 4. The medical device of any one of Embodiments 1 to 3, wherein the first material comprises a paramagnetic material and the second material comprises a ferromagnetic material.

Embodiment 5. The medical device of any one of Embodiments 1 to 4, wherein the first material comprises a Cobalt Chromium alloy.

Embodiment 6. The medical device of Embodiment 3, wherein the first material comprises a Nickel Cobalt alloy.

Embodiment 7. The medical device of any preceding Embodiment, wherein the second material is iron or an alloy containing iron.

Embodiment 9. The medical device of any preceding Embodiment, wherein the reinforcement member comprises a coil.

Embodiment 10. The medical device of Embodiment 9, wherein the coil is a flat wire coil.

Embodiment 11. The medical device of Embodiment 10, wherein the flat wire coil has a thickness in the range of about 0.03 mm to about 0.15 mm and/or a width in the range of about 0.25 mm to about 0.5 mm.

Embodiment 12. The medical device of Embodiment 10 or 11, wherein the first material has a magnetic susceptibility in the range of about 1 ppm to about 3000 ppm, or about 1 ppm to about 2000 ppm, or about 1 ppm to about 1000 ppm.

Embodiment 13. The medical device of any one of Embodiments 1 to 7, wherein the reinforcement member comprises a mesh.

Embodiment 14. The medical device of Embodiment 1, wherein the passive MRI marker comprises a band of the second material.

Embodiment 15. The medical device of any preceding Embodiment, wherein the passive MRI marker is disposed between the inner tubular member and the outer tubular member.

Embodiment 16. The medical device of Embodiment 15, wherein the passive MRI marker is disposed distal to the reinforcement member.

Embodiment 17. The medical device of Embodiment 15, wherein the passive MRI marker is disposed at a position that longitudinally coincides with a segment of the reinforcement member.

Embodiment 18. The medical device of Embodiment 17, wherein the passive MRI marker is at least in part positioned between the inner tubular member and the reinforcement member.

Embodiment 19. The medical device of Embodiment 18, wherein the second material of the passive MRI marker is in a layer deposited on an outer surface of the inner tubular member.

Embodiment 20. The medical device of Embodiment 19, wherein the inner tubular member is formed of a fluoropolymer, and wherein the outer surface of the inner tubular member is a roughened outer surface; optionally, wherein the roughened outer surface is a chemically etched outer surface.

Embodiment 21. The medical device of any preceding Embodiment, wherein the passive MRI marker has a maximum thickness that is less than that of the reinforcement member.

Embodiment 22. The medical device of any preceding Embodiment, where the passive MRI marker has a longitudinal length along the elongate member not exceeding 10 mm, or not exceeding 5 mm, or not exceeding 3 mm.

Embodiment 23. The medical device of Embodiment 17, wherein the passive MRI marker is at least in part positioned between an outer surface of the reinforcement member and the outer tubular member.

Embodiment 24. The medical device of Embodiment 23, wherein the second material of the passive MRI marker is in a layer deposited at least in part on the outer surface of the reinforcement member; optionally, wherein the layer is also deposited at least in part on an outer surface of the inner tubular member.

Embodiment 25. The medical device of Embodiment 24, wherein the inner tubular member is formed of a fluoropolymer, and wherein the outer surface of the inner tubular member is a roughened outer surface; optionally, wherein the roughened outer surface is a chemically etched outer surface.

Embodiment 26. The medical device of Embodiment 18, wherein the passive MRI marker is at least in part, or is entirely, positioned between coil turns of the reinforcement member; optionally wherein the passive MRI marker has a thickness not exceeding a thickness of the reinforcement member.

Embodiment 27. The medical device of any one of Embodiments 24 to 26, wherein the passive MRI marker has a longitudinal length along the elongate member not exceeding 10 mm, or not exceeding 5 mm, or not exceeding 3 mm.

Embodiment 28. The medical device of any one of Embodiments 1 to 27, wherein the outer tubular member has been thermoformed against and around the reinforcement member and against the passive MRI marker and an outer surface of the inner tubular member.

Embodiment 29. The medical device of any one of Embodiments 1 to 13, wherein the passive MRI marker is disposed within a thermoformed polymeric material providing a distal tip of the elongate member; optionally, wherein the passive MRI marker is in the form of a plug of the second material.

Embodiment 30. The medical device of Embodiment 1, wherein:

the inner tubular member is formed of a lubricious fluoropolymer;

the outer tubular member is formed of a thermoformable polymeric material that has been thermoformed against and around the reinforcement member and against an outer surface of the inner tubular member;

the inner tubular member has a first longitudinal segment that longitudinally co-extends with the reinforcement member along the elongate member;

the inner tubular member has a second longitudinal segment distal of a distal end of the reinforcement member, the second longitudinal segment having an outer surface; and the elongate member includes a thermoformed polymeric material providing a distal tip of the elongate member extending distally beyond a distal end of the inner tubular member; optionally, wherein the thermoformed polymeric material is bonded to the outer surface of the second longitudinal segment of the inner tubular member.

Embodiment 31. The medical device of Embodiment 30, wherein the passive MRI marker is disposed between the inner tubular member and the outer tubular member, and the outer tubular member has also been thermoformed against the reinforcement member.

Embodiment 32. The medical device of Embodiment 30, wherein the passive MRI marker is disposed in the thermoformed polymeric material providing the distal tip of the elongate member.

Embodiment 33. The medical device of Embodiment 31, also comprising a second passive MRI marker, wherein the second passive MRI marker is disposed in the thermoformed polymeric material providing the distal tip of the elongate member.

Embodiment 34. The medical device of any one of Embodiments 30 to 33, wherein the first material has a magnetic susceptibility not exceeding about 3000 ppm, or not exceeding about 2000 ppm, or not exceeding about 1000 ppm.

Embodiment 35. The medical device of any one of Embodiments 30 to 34, wherein the second material has a magnetic susceptibility of at least about 500 ppm, or at least about 2000 ppm, or at least about 7000 ppm, or in the range of about 500 ppm to about 1,000,000, or in the range of about 7000 ppm to about 100,000; optionally wherein the magnetic susceptibility of the second material is greater than the magnetic susceptibility of the first material.

Embodiment 36. The medical device of any one of Embodiments 30 to 35, wherein the first material is selected from Titanium, Nickel-containing alloys, Cobalt-containing alloys, Cobalt Chromium alloys, tungsten, and a polymeric material; optionally, wherein the Nickel-containing alloy is a Nickel-Titanium, a Nickel-Cobalt alloy, or a Nickel-Chromium alloy.

Embodiment 37. The medical device of any one of Embodiments 30 to 36, wherein the second material is selected from nickel, alloys of nickel, iron, alloys of iron, cobalt, and alloys of cobalt.

Embodiment 38. The medical device of any one of Embodiments 30 to 37, wherein the outer tubular member is formed of a thermoformable polyamide polymer.

Embodiment 39. The medical device of any one of Embodiments 30 to 38, wherein the thermoformed polymeric material providing the distal tip is a thermoformed polyamide material.

Embodiment 40. The medical device of any one of Embodiments 30 to 39, wherein the lubricous fluoropolymer is polytetrafluoroethylene.

Embodiment 41. The medical device of any one of Embodiments 30 to 40, which is an introducer sheath.

Embodiment 42. The medical device of Embodiment 41, also comprising a proximal hub including an elastomeric seal member for preventing backflow of fluids through the hub.

Embodiment 43. The medical device of Embodiment 41 or 42, wherein the proximal hub also includes a side arm configured for connection to a polymeric tube.

Embodiment 44. The medical device of any one of Embodiments 30 to 43, wherein the circumferential wall has a wall thickness in the range of about 0.25 mm to about 0.35 mm.

Embodiment 45. The medical device of any one of Embodiments 30 to 44, wherein the first material is a superalloy containing nickel, cobalt, chromium and molybdenum.

Embodiment 46. A method for making a medical device, comprising:

positioning an elongate reinforcement member around an elongate polymeric inner tubular member, the reinforcement member being formed from a first material having a first magnetic susceptibility;

positioning an elongate thermoformable polymeric outer tubular member around the reinforcement member and inner tubular member;

thermoforming the outer tubular member against and around the reinforcement member and against an outer surface of the inner tubular member to provide an elongate reinforced tubular structure; and attaching a passive MRI marker formed from a second material to the reinforced tubular structure, the second material having a magnetic susceptibility that is different than, preferably greater than, the first magnetic susceptibility.

Embodiment 47. The method of Embodiment 46, wherein said attaching comprises positioning the passive MRI marker between the inner tubular member and the outer tubular member prior to said thermoforming.

Embodiment 48. The method of Embodiment 46, also comprising thermoforming a distal tip that extends beyond a distal end of the inner tubular member, the distal tip comprised of a thermoformed volume of polymeric material.

Embodiment 49. The method of Embodiment 48, wherein the thermoformed volume of polymeric material is a polyamide material.

Embodiment 50. The method of Embodiment 48 or 49, wherein said attaching comprises disposing the passive MRI marker in the thermoformed volume of polymeric material.

Embodiment 51. The method of any one of Embodiments 46 to 50, wherein the first material has a magnetic susceptibility not exceeding 3000 ppm, or not exceeding about 2000 ppm, or not exceeding about 1000 ppm.

Embodiment 52. The method of any one of Embodiments 46 to 51, wherein the second material has a magnetic susceptibility of at least about 500 ppm, or at least about 2000 ppm, or at least about 7000 ppm, or in the range of about 500 ppm to about 1,000,000, or in the range of about 7000 ppm to about 100,000; optionally, wherein the magnetic susceptibility of the second material is greater than the magnetic susceptibility of the first material.

Embodiment 53. The method of any one of Embodiments 46 to 52, wherein the first material is selected from Titanium, Nickel-containing alloys, Cobalt-containing alloys, Cobalt Chromium alloys, tungsten, and a polymeric material; optionally, wherein the Nickel-containing alloy is a Nickel-Titanium, a Nickel-Cobalt alloy, or a Nickel-Chromium alloy.

Embodiment 54. The method of any one of Embodiments 46 to 53, wherein the second material is selected from nickel, alloys of nickel, iron, alloys of iron, cobalt, and alloys of cobalt.

Embodiment 55. The method of any one of Embodiments 46 to 54, wherein the medical device is an introducer sheath.

Embodiment 56. The method of Embodiment 55, also comprising providing a proximal hub on the medical device, wherein the proximal hub includes an elastomeric seal member for preventing backflow of fluids through the hub.

Embodiment 57. The method of any one of Embodiments 46 to 56, wherein the circumferential wall has a wall thickness in the range of about 0.25 mm to about 0.35 mm.

Embodiment 58. The method of any one of Embodiments 46 to 57, wherein the first material is a superalloy containing nickel, cobalt, chromium and molybdenum.

Embodiment 59. A method for treating a patient, comprising:

- inserting a medical device according to any one of Embodiments 1 to 45 into a region in a patient; and
- obtaining an MRI image of the region while the passive MRI marker of the medical device is positioned in the region.

Embodiment 60. The method of Embodiment 59, wherein the medical device is an introducer sheath, and wherein said inserting comprises percutaneously inserting the introducer sheath.

Embodiment 61. A medical device, comprising:

- an elongate member having a proximal end, a distal end, and a circumferential wall having an outer surface and an inner surface that defines a lumen;
- a reinforcement member disposed within the circumferential wall, extending along a length of the elongate member, and formed of a first material and having a first susceptibility; and
- a marker attached to the elongate member and formed of a second material and having a second susceptibility that is different from the first susceptibility.

Embodiment 62. The medical device of Embodiment 61, wherein the first material and the second material are the same.

Embodiment 63. The medical device of Embodiment 61, wherein the first material and the second material are different.

Embodiment 64. The medical device of Embodiment 63, wherein the first material comprises a paramagnetic material and the second material comprises a ferromagnetic material.

Embodiment 65. The medical device of Embodiment 63, wherein the first material comprises an alloy containing less than or equal to 1% Iron by weight and the second material comprises an alloy containing at least 50% Iron by weight.

Embodiment 66. The medical device of Embodiment 63, wherein the first material comprises a Cobalt Chromium alloy and the second material comprises a stainless steel alloy Embodiment 67. The medical device of Embodiment 63, wherein the first material comprises a Nickel Cobalt alloy and the second material comprises a stainless steel alloy.

Embodiment 68. The medical device of Embodiment 67, wherein the second material comprises one of 304V stainless steel and 316LVM stainless steel.

Embodiment 69. The medical device of Embodiment 61, wherein the reinforcement member comprises a coil.

Embodiment 70. The medical device of Embodiment 61, wherein the reinforcement member comprises a mesh.

Embodiment 71. The medical device of Embodiment 61, wherein the marker comprises a band.

Embodiment 72. The medical device of Embodiment 61, wherein the marker comprises a twisted ring.

Embodiment 73. The medical device of Embodiment 61, wherein the marker is disposed within the circumferential wall.

Embodiment 74. The medical device of Embodiment 61, wherein the marker is disposed distal to the reinforcement member.

Embodiment 75. The medical device of Embodiment 61, wherein the marker comprises a first marker; and further comprising a second marker formed of a third material and having a third susceptibility that is different from the first susceptibility.

Embodiment 76. The medical device of Embodiment 75, wherein the first marker is disposed distal to the reinforcement member.

Embodiment 77. The medical device of Embodiment 75, wherein the second marker is disposed distal to the reinforcement member.

Embodiment 78. A medical device, comprising:

- an elongate member having a proximal end, a distal end, and a circumferential wall having an outer surface and an inner surface that defines a lumen;
- a reinforcement member disposed within the circumferential wall, extending along a length of the elongate member, and formed of a first material having a first magnetic susceptibility; and
- a marker disposed within the circumferential wall distal to the reinforcement member and formed of a second material different from the first material and having a second magnetic susceptibility that is different than, preferably greater than, the first magnetic susceptibility.

Embodiment 79. The medical device of Embodiment 78, wherein the second material comprises one of 304V stainless steel and 316LVM stainless steel.

Embodiment 80. A medical device, comprising:

- an elongate member having a proximal end, a distal end, and a circumferential wall having an outer surface and an inner surface that defines a lumen;
- a reinforcement member comprising a coil disposed within the circumferential wall, extending along a length of the elongate member, and formed of a first material having a first magnetic susceptibility; and
- a marker disposed within the circumferential wall distal to the reinforcement member and formed of a second material different from the first material and having a second magnetic susceptibility that is greater than the first magnetic susceptibility.

Embodiment 81. The medical device of Embodiment 61, wherein the first material is a Nickel Cobalt alloy.

Embodiment 82. The medical device of Embodiment 61 or 81, wherein the reinforcement member is a coil or a mesh of wires.

Embodiment 83. The medical device of Embodiment 82, wherein the elongate member has a distal portion free of the reinforcement member.

Embodiment 84. The medical device of Embodiment 83, wherein the marker is in the distal portion of the elongate member and axially spaced from a distal end of the reinforcement member.

Embodiment 85. The medical device of Embodiment 84, wherein the marker is disposed within the circumferential wall of the elongate member.

Embodiment 86. The medical device of Embodiment 85, wherein the circumferential wall comprises a liner formed of a lubricious fluoropolymer providing the inner surface defining the lumen, with the inner surface occurring radially inward of the marker.

Embodiment 87. The medical device of Embodiment 86, wherein the circumferential wall also comprises a polyamide polymer.

Embodiment 88. The medical device of any one of Embodiments 81 to 87, wherein the marker comprises stainless steel.

Embodiment 89. The medical device of any one of Embodiment 81 to 88, wherein the marker provides a first marker, and wherein the device also includes a second marker formed of a third material having a third susceptibility that is different from the first susceptibility.

Embodiment 90. The medical device of Embodiment 89, wherein the second marker comprises stainless steel.

Embodiment 91. The medical device of any one of Embodiments 81 to 90, wherein the reinforcement member is a coil.

Embodiment 92. The medical device of any one of Embodiments 81 to 90, wherein the reinforcement member is a mesh.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A medical device, comprising:

an elongate member having a proximal end, a distal end, and a circumferential wall having an outer surface and an inner surface that defines a lumen, wherein the circumferential wall includes an inner tubular member formed of a first polymeric material and an outer tubular member formed of a second polymeric material;

a reinforcement member disposed within the circumferential wall between the inner tubular member and the outer tubular member, extending along a length of the elongate member, and formed of a first material and having a first magnetic susceptibility; and a passive magnetic resonance imaging (MRI) marker attached to the elongate member and formed of a second material having a second magnetic susceptibility that is different than the first magnetic susceptibility.

2. The medical device of claim 1, wherein the first material comprises a paramagnetic material and the second material comprises a ferromagnetic material.

3. The medical device of claim 1, wherein the first material comprises a Cobalt Chromium alloy or a Nickel Cobalt alloy.

4. The medical device of claim 1, wherein the passive MRI marker is disposed between the inner tubular member and the outer tubular member, and wherein the passive MRI marker is disposed at a position that longitudinally coincides with a segment of the reinforcement member.

5. The medical device of claim 1, wherein the outer tubular member has been thermoformed against and around the reinforcement member and against the passive MRI marker and an outer surface of the inner tubular member.

6. The medical device of claim 1, wherein the passive MRI marker is disposed within a thermoformed polymeric material providing a distal tip of the elongate member.

7. A method for treating a patient, comprising:

inserting a medical device according to claim 1 into a region in a patient; and obtaining an MRI image of the region while the passive MRI marker of the medical device is positioned in the region.

8. The medical device of claim 1, wherein the second magnetic susceptibility is greater than the first magnetic susceptibility.

9. The medical device of claim 1, wherein the first material has a magnetic susceptibility not exceeding 3000 ppm and the second material has a magnetic susceptibility of at least 7000 ppm.

10. The medical device of claim 9, wherein the reinforcement member comprises a mesh.

11. The medical device of claim 9, wherein the reinforcement member comprises a coil.

12. The medical device of claim 11, wherein the coil is a flat wire coil having a thickness in the range of 0.03 mm to 0.15 mm and a width in the range of 0.25 mm to 0.5 mm.

13. The medical device of claim 1, wherein the passive MRI marker comprises a band of the second material.

14. The medical device of claim 13, wherein the passive MRI marker is disposed between the inner tubular member and the outer tubular member and distal to the reinforcement member.

15. A medical device, comprising:

an elongate member having a proximal end, a distal end, and a circumferential wall having an outer surface and an inner surface that defines a lumen, wherein the circumferential wall includes an inner tubular member formed of a first polymeric material and an outer tubular member formed of a second polymeric material;

a reinforcement member disposed within the circumferential wall between the inner tubular member and the outer tubular member, extending along a length of the elongate member, and formed of a first material and having a first magnetic susceptibility not exceeding 3000 ppm;

a passive magnetic resonance imaging (MRI) marker attached to the elongate member and formed of a second material having a second magnetic susceptibility that is greater than the first magnetic susceptibility;

wherein the inner tubular member is formed of a lubricious fluoropolymer;

wherein the outer tubular member is formed of a thermoformable polymeric material that has been thermoformed against and around the reinforcement member and against an outer surface of the inner tubular member;

wherein the inner tubular member has a first longitudinal segment that longitudinally co-extends with the reinforcement member along the elongate member;

wherein the inner tubular member has a second longitudinal segment distal of a distal end of the reinforcement member, the second longitudinal segment having an outer surface; and wherein the elongate member includes a thermoformed polymeric material providing a distal tip of the elongate member extending distally beyond a distal end of the inner tubular member.

16. The medical device of claim 15, wherein the passive MRI marker is disposed in the thermoformed polymeric material providing the distal tip of the elongate member.

17. The medical device of claim 15, wherein the second material has a magnetic susceptibility of at least 7000 ppm.

18. The medical device of claim 15, wherein the circumferential wall has a wall thickness in the range of 0.25 mm to 0.35 mm.

19. The medical device of claim 15, wherein the first material is a superalloy containing nickel, cobalt, chromium and molybdenum.

20. The medical device of claim 15, wherein the thermoformed polymeric material is bonded to the outer surface of the second longitudinal segment of the inner tubular member.

21. The medical device of claim 15, wherein the passive MRI marker is disposed between the inner tubular member and the outer tubular member, and the outer tubular member has also been thermoformed against the passive MRI marker.

22. The medical device of claim 21, also comprising a second passive MRI marker, wherein the second passive MRI marker is disposed in the thermoformed polymeric material providing the distal tip of the elongate member.

23. The medical device of claim 21, wherein the first material has a magnetic susceptibility not exceeding 2000 ppm.

24. The medical device of claim 15, wherein the first material is selected from Titanium, Nickel-containing alloys, Cobalt-containing alloys, Cobalt Chromium alloys, tungsten, and a polymeric material.

25. The medical device of claim 24, wherein the second material is selected from nickel, alloys of nickel, iron, alloys of iron, cobalt, and alloys of cobalt.

26. The medical device of claim 25, wherein the outer tubular member is formed of a thermoformable polyamide polymer, and wherein the thermoformed polymeric material providing the distal tip is a thermoformed polyamide material.

27. The medical device of claim 26, wherein the lubricous fluoropolymer is polytetrafluoroethylene.

28. The medical device of claim 27, which is an introducer sheath comprising a proximal hub including an elastomeric seal member for preventing backflow of fluids through the hub.

29. A method for making a medical device, comprising:

positioning an elongate reinforcement member around an elongate polymeric inner tubular member, the reinforcement member being formed from a first material having a first magnetic susceptibility;

positioning an elongate thermoformable polymeric outer tubular member around the reinforcement member and inner tubular member;

thermoforming the outer tubular member against and around the reinforcement member and against an outer surface of the inner tubular member to provide an elongate reinforced tubular structure; and attaching a passive magnetic resonance imaging (MRI) marker formed from a second material to the reinforced tubular structure, the second material having a magnetic susceptibility that is different than the first magnetic susceptibility.

30. The method of claim 29, wherein the second magnetic susceptibility is greater than the first magnetic susceptibility.

* * * * *